US010914746B2

United States Patent
Lema Gesto et al.

(10) Patent No.: US 10,914,746 B2
(45) Date of Patent: Feb. 9, 2021

(54) BIOMARKERS FOR DIAGNOSIS AND PROGNOSIS OF CORNEAL ECTATIC DISORDERS

(71) Applicants: UNIVERSIDADE DE SANTIAGO DE COMPOSTELA, A Coruña (ES); SERVIZO GALEGO DE SAUDE (SERGAS), A Coruña (ES)

(72) Inventors: María Isabel Lema Gesto, A Coruña (ES); José Antonio Castillo Sánchez, A Coruña (ES); Tomás Sobrino Moreiras, A Coruña (ES); Francisco Campos Perez, A Coruña (ES)

(73) Assignees: UNIVERSIDADE DE SANTIAGO DE COMPOSTELA, A Coruña (ES); SERVIZO GALEGO DE SAUDE (SERGAS), A Coruña (ES)

(*) Notice: Subject to any disclaimer, the term of this patent is extended or adjusted under 35 U.S.C. 154(b) by 0 days.

(21) Appl. No.: 15/551,386

(22) PCT Filed: Feb. 16, 2016

(86) PCT No.: PCT/EP2016/053293
§ 371 (c)(1),
(2) Date: Aug. 16, 2017

(87) PCT Pub. No.: WO2016/131840
PCT Pub. Date: Aug. 25, 2016

(65) Prior Publication Data
US 2018/0067128 A1 Mar. 8, 2018

(30) Foreign Application Priority Data
Feb. 16, 2015 (EP) .................................... 15382060

(51) Int. Cl.
*G01N 33/50* (2006.01)
*G01N 33/53* (2006.01)
*G01N 33/577* (2006.01)
*G01N 33/68* (2006.01)
*C12Q 1/68* (2018.01)
*C07K 14/705* (2006.01)
*C12Q 1/6876* (2018.01)

(52) U.S. Cl.
CPC ....... *G01N 33/6893* (2013.01); *C07K 14/705* (2013.01); *C07K 14/70596* (2013.01); *C12Q 1/68* (2013.01); *C12Q 1/6876* (2013.01); *G01N 33/50* (2013.01); *G01N 33/5044* (2013.01); *G01N 33/53* (2013.01); *G01N 33/577* (2013.01); *G01N 33/68* (2013.01); *G01N 2800/16* (2013.01)

(58) Field of Classification Search
CPC ...... G01N 33/50; G01N 33/53; G01N 33/577; G01N 33/68; G01N 33/6893; G01N 2800/16; C07K 14/705; C07K 14/70596; C12Q 1/68; C12Q 1/6876
See application file for complete search history.

(56) References Cited

U.S. PATENT DOCUMENTS

| 2007/0248970 | A1 | 10/2007 | Rabinowitz et al. |
| 2009/0317831 | A1* | 12/2009 | Brown ............ G01N 33/56911 435/7.21 |
| 2013/0058954 | A1* | 3/2013 | Sutton .................. A61K 31/437 424/172.1 |

FOREIGN PATENT DOCUMENTS

| WO | 2011/066621 A1 | 6/2011 |
| WO | 2013/107826 A2 | 7/2013 |
| WO | WO-2014106833 A1 * | 7/2014 |

OTHER PUBLICATIONS

Bitko et al. Activation of cytokines and NF-kappa B in corneal epithelial cells infected by respiratory syncytial virus: potential relevance in ocular inflammation and respiratory infection. BMC Microbiol 4: 28, 2004; 11 total pages.*
Brignole et al. Flow cytometric analysis of inflammatory markers in conjunctival epithelial cells of patients with dry eyes. Invest Ophthalmol Vis Sci 41: 1356-1363, 2000.*
Karamichos et al. In vitro model suggests oxidative stress involved in keratoconus disease. Sci Reports 4: 4608, 2014; 7 total pages.*
Redfern et al. Toll-like receptors in ocular surface disease. Exp Eye Res 90: 679-687, 2010.*
Shetty et al. Attenuation of lysyl oxidase and collagen gene expression in keratoconus patient corneal epithelium corresponds to disease severity. Mol Vision 21: 12-25, published Jan. 12, 2015.*
Sobrino et al. Higher expression of Toll-like receptors 2 and 4 in blood cells of keratoconus patients. Sci Reports 7: 12975, 2017; 7 total pages.*
Bromley et al. Treatment strategies for corneal ectasia. Curr Opin Ophthalmol 21: 255-258, 2010.*
Gomes et al. Global consensus on keratoconus and ectatic diseases. Cornea 34: 359-369, 2015.*
McMahon et al., "Longitudinal Changes in Corneal Curvature in Keratoconus", Cornea, Apr. 2006, pp. 296-305, vol. 25, No. 3.
Rabinowitz, "Keratoconus", Survey of Ophthalmology, Jan.-Feb. 1998, pp. 297-319, vol. 42, No. 4.

(Continued)

*Primary Examiner* — Bridget E Bunner
(74) *Attorney, Agent, or Firm* — Thompson Coburn LLP; William A. Holtz

(57) ABSTRACT

The invention relates to the field of the diagnosis and prognosis methods of molecular pathologies. In particular, the invention relates to methods for determining the diagnosis of an ectatic disease of the cornea in a subject, for determining the risk of developing an ectatic disease of the cornea in a subject, for determining the clinical outcome of a subject suffering from an ectatic disease of the cornea and for selecting a subject to be treated with a therapy for an ectatic disease of the cornea based on the determination of the expression levels of TLR2 and/or TLR4 markers. The invention also relates to the use of the TLR2 and/or TLR4 as diagnosis and prognosis markers for an ectatic disease of the cornea.

14 Claims, 5 Drawing Sheets

(56) References Cited

OTHER PUBLICATIONS

Wagner et al., "Collaborative Longitudinal Evaluation of Keratoconus (CLEK) Study: Methods and Findings to Date", Contact Lens and Anterior Eye, 2007, pp. 223-232, vol. 30.
Lambiase et al., "Toll-Like Receptors in Ocular Surface Diseases: Overview and New Findings", Clinical Science, May 1, 2011, pp. 441-450, vol. 120.
European Search Report for Application 15382060.0 dated Dec. 7, 2015.
International Search Report for PCT/EP2016/053293 dated May 27, 2016.
Johnson et al., "Activation of Toll-Like Receptor (TLR)2, TLR4, and TLR9 in the Mammalian Cornea Induces MyD88-Dependent Corneal Inflammation", Investigative Ophthalmology & Visual Science, Feb. 1, 2005, pp. 589-595, vol. 46, No. 2.
Li et al., "Pretreatment with TLR2 and TLR4 Ligand Modulates Innate Immunity in Corneal Fibroblasts Challenged with Aspergillus Fumigatus", Jun. 2013, pp. 4261-4270, vol. 54, No. 6.
Micera et al., "Toll-Like Receptors and the Eye", Current Opinion in Allergy and Clinical Immunology, Jan. 1, 2005, pp. 451-458, vol. 5, No. 5.
Rumelt, "Advances in Opthalmology", Mar. 2012, 570 pages.
Yuan et al., "Toll-Like Receptors Involved in the Pathogenesis of Experimental Candida Albicans Keratitis", Investigative Opthalmology & Visual Science, Apr. 1, 2010, pp. 2094-2100, vol. 51, No. 4.
Erdinest et al., "Expression and Activation of Toll-Like Receptor 3 and Toll-Like Receptor 4 on Human Corneal Epithelial and Conjuctival Fibroblasts", Journal of Inflammation, 2014, 10 pages, vol. 11, No. 3.
Liu et al., "Higher Expression of Toll-like Receptors 2, 3, 4, and 8 in Ocular Behcet's Disease", Investigative Ophthalmology & Visual Science, Sep. 2013, pp. 6012-6017, vol. 54, No. 9.
Mai et al., "Role of Toll-like Receptors in Human Iris Pigment Epithelial Cells and Their Response to Pathogen-associated Molecular Patterns", Journal of Inflammation, 2014, 12 pages, vol. 11, No. 20.
Sutton et al., "Laser in Situ Keratomileusis in 2012: A Review", Clinical and Experimental Optometry, 2014, pp. 18-29, vol. 97.
English Translation of Japan Office Action, 2017-561040, dated Nov. 5, 2019.
Goldberg, "Preoperative Evaluation of Patients Before Cataract and Refractive Surgery", International Ophthalmology Clinics, 2011, pp. 97-107, vol. 51, No. 2.
Sadaka et al., "Bacterial Endophthalmitis in the Age of Outpatient Intravitreal Therapies and Cataract Surgeries: Host-Microbe Interactions in Intraocular Infection", Progress in Retinal and Eye Research, 2012, pp. 316-331, vol. 31.
Williams, "Role of MAL/TIRAP in TLR2- and TLR4-, but not TLR5-Induced Corneal Inflammation", 2010, Retrieved from the internet, 70 pages.
Ueda et al., "167 Intracellular Expression of TLR2 and TLR4 in Corneal Epithelium", Journal of Japanese Opthalmological Society, 2003, p. 216, vol. 107.

\* cited by examiner

BIOMARKERS FOR DIAGNOSIS AND PROGNOSIS OF CORNEAL ECTATIC DISORDERS

CROSS-REFERENCE TO RELATED APPLICATIONS

This application is a U.S. National Phase application of PCT/EP2016/053293, filed on Feb. 16, 2016, claiming the benefit of European Application No. 15382060.0, filed Feb. 16, 2015, both of which are incorporated herein by reference in their entireties.

FIELD OF THE INVENTION

The invention relates to the field of molecular diagnosis and prognosis methods for pathologies. In particular, the invention relates to methods for determining the diagnosis of an ectatic disease of the cornea in a subject, for determining the risk of developing an ectatic disease of the cornea in a subject, for determining the clinical outcome of a subject suffering from an ectatic disease of the cornea and for selecting a subject to be treated with a therapy for an ectatic disease of the cornea based on the determination of the expression levels of toll-like receptors (TLR) TLR2 and/or TLR4 markers. The invention also relates to the use of the TLR2 and/or TLR4 as diagnostic and prognostic markers for an ectatic disease of the cornea.

BACKGROUND OF THE INVENTION

Corneal ectasia is a progressive disease that adversely affects the structural integrity of the cornea. The weakened cornea bulges, and crippling irregular astigmatism starts to develop. The astigmatism degrades vision and as the disease progresses, scarring of the cornea occurs. Corneal ectasia includes keratoconus, pellucid marginal degeneration, post-refractive surgery ectasia, and other rare diseases such as keratoglobus. New modalities for the treatment of corneal ectasia have been developed, such as corneal collagen cross-linkage that uses UV light and Riboflavin to stiffen the cornea and halt the progression of the disease. It is desirable to halt the progression of the disease at a very early stage, before vision is degraded by irregular astigmatism or scarring. The most common cause of the post-refractive surgery ectasia that threatens vision in those patients is performing the refractive surgery on an early ectasia patient who was not detected by the conventional current diagnostic techniques. This highlights the need for a specific and sensitive sign that can be used to detect those early patients to save them from such a devastating complication.

Corneal topography and thickness are among the current diagnostic criteria of ectasia. Their use is complicated by their variations among the general populations. Normal range of corneal thicknesses is wide, and overlapping between normal thin corneas and early ectasia patients complicates the use of this criterion in the diagnosis of early cases of ectasia. Thus, lack of specificity is a significant limitation of using corneal thickening for the diagnosis of the ectasia. Corneal topography use in diagnosis of ectasia shares the same limitations as corneal thinning. Irregular astigmatism is seen in normal subjects and in ectasia patients complicating its use to make the diagnosis, especially in mild cases.

Innovative orientation of the research is necessary in this context to provide biomarkers for diagnosing corneal ectasia in a subject as well as for determining the risk of onset and the progression of said disease.

BRIEF DESCRIPTION OF THE INVENTION

In a first aspect, in vitro method for diagnosing an ectatic disease of the cornea in a subject which comprises:
a) determining the expression level of TLR2 and/or TLR4 in a sample from said subject; and
b) comparing said expression level with a reference value wherein, if the expression level of TLR2 and/or TLR4 is higher than said reference value is indicative that the subject suffers from an ectatic disease of the cornea.

In another aspect, the invention relates to an in vitro method for determining the risk of developing an ectatic disease of the cornea in a subject which comprises:
a) determining the expression level of TLR2 and/or TLR4 in a sample from said subject; and
b) comparing said expression level with a reference value. wherein, if the expression level of TLR2 and/or TLR4 is higher than said reference value is indicative that the subject has high risk of developing an ectatic disease of the cornea.

In another aspect, the invention relates to an in vitro method for determining the clinical outcome of a subject suffering from an ectatic disease of the cornea, comprising:
a) determining the expression level of TLR2 and/or TLR4 in a sample from said subject; and
b) comparing said expression level with a reference value wherein if the expression level of TLR2 and/or TLR4 is higher than said reference value is indicative of a negative clinical outcome.

In another aspect, the invention relates to an in vitro method for selecting a subject to be treated with a therapy for an ectatic disease of the cornea which comprises:
a) determining the expression level of TLR2 and/or TLR4 in a sample from said subject; and
b) comparing said expression level with a reference value wherein if the expression level of TLR2 and/or TLR4 is higher than said reference value is indicative that said subject is candidate to be treated with a therapy for an ectatic disease of the cornea.

In another aspect the invention relates to the use of TLR2 and/or TLR4 as a marker for determining the diagnosis of an ectatic disease of the cornea in a subject.

In another aspect, the invention relates to the use of TLR2 and/or TLR4 as a marker for determining the risk of developing an ectatic disease of the cornea in a subject.

In another aspect, the invention relates to the use of TLR2 and/or TLR4 as a marker for determining the clinical outcome of a subject suffering from an ectatic disease of the cornea.

Finally, in another aspect, the invention relates to the use of TLR2 and/or TLR4 as a marker for selecting a subject to be treated with a therapy for an ectatic disease of the cornea.

DETAILED DESCRIPTION OF THE INVENTION

Figure 1:
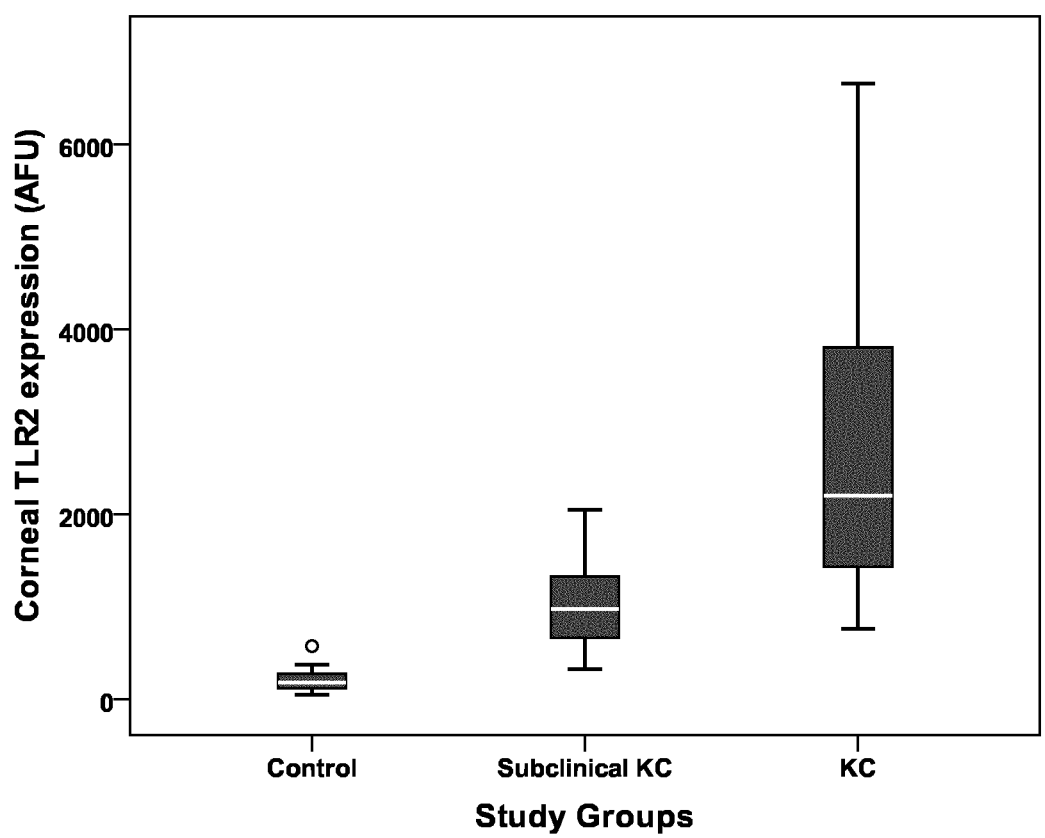
FIG. 1: Median [quartiles] of TLR2 expression levels in corneal cells by study groups in cohort A. A gradual increase in the expression of TLR2 is observed in a corneal ectasia as keratoconus compared to control subjects: Control<Subclinical keratoconus<keratoconus.
Figure 2:
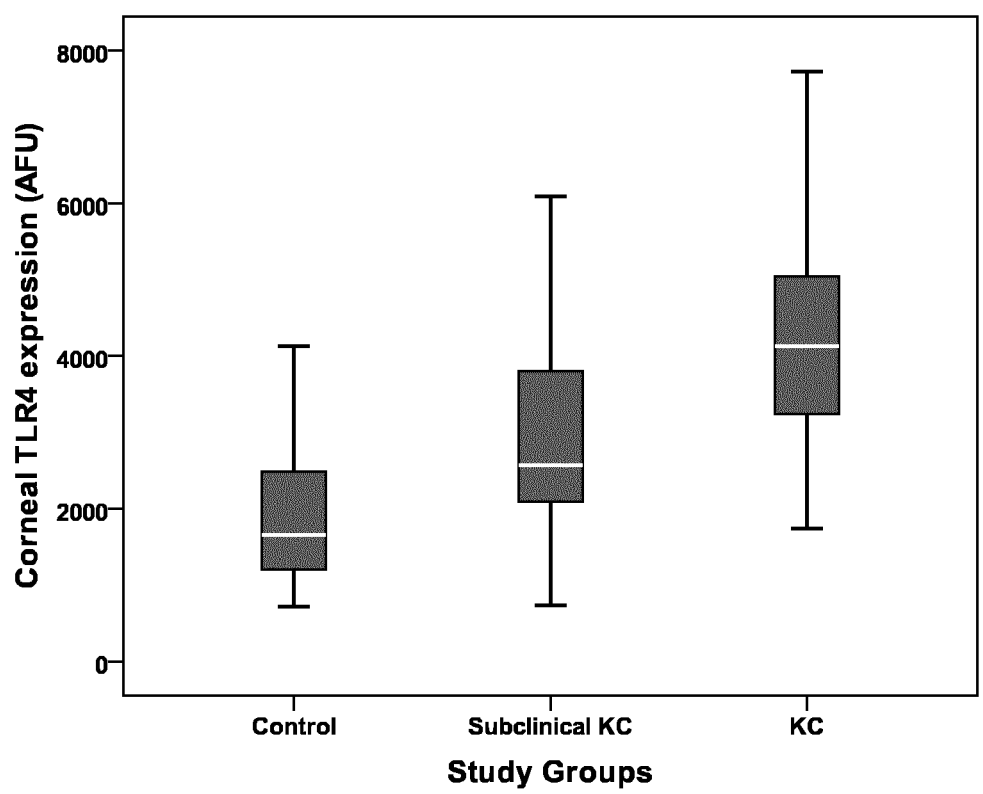
FIG. 2: Median [quartiles] of TLR4 expression levels in corneal cells by study groups in cohort A. A gradual increase in the expression of TLR2 is observed in a corneal ectasia as keratoconus compared to control subjects: Control<Subclinical keratoconus<keratoconus.
Figure 3:
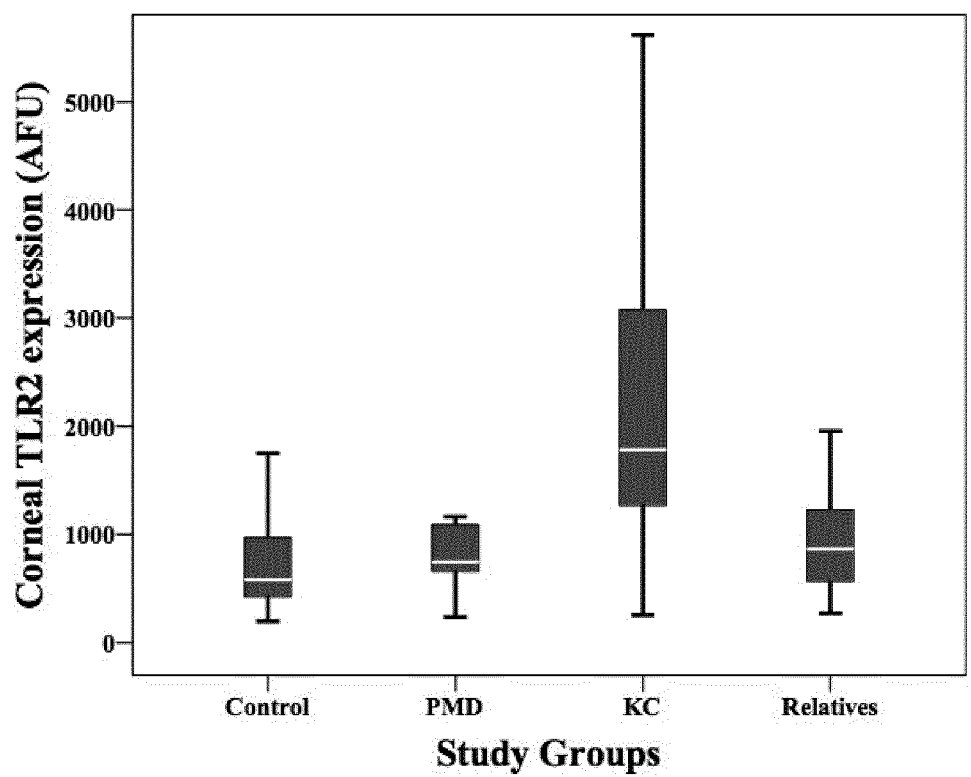
FIG. 3: Median [quartiles] of TLR2 expression levels in corneal cells by study groups in cohort B. A gradual increase in the expression of TLR2 is observed: Control<Relatives<keratoconus. Likewise, keratoconus (KC) patients showed a higher expression of TLR2 in corneal cells than pellucid marginal degeneration (PMD) patients.
Figure 4:
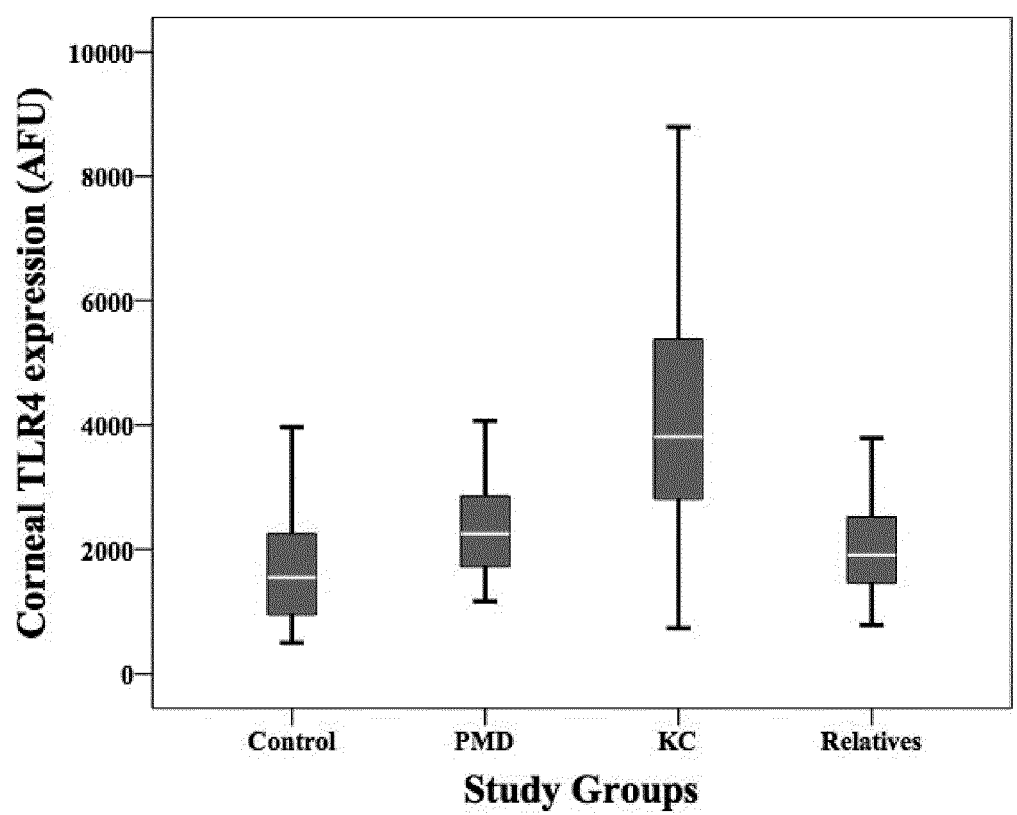
FIG. 4: Median [quartiles] of TLR4 expression levels in corneal cells by study groups in cohort B. A gradual increase in the expression of TLR4 is observed: Control<Relatives<keratoconus. Likewise, keratoconus (KC) patients showed a higher expression of TLR4 in corneal cells than pellucid marginal degeneration (PMD) patients.
Figure 5:
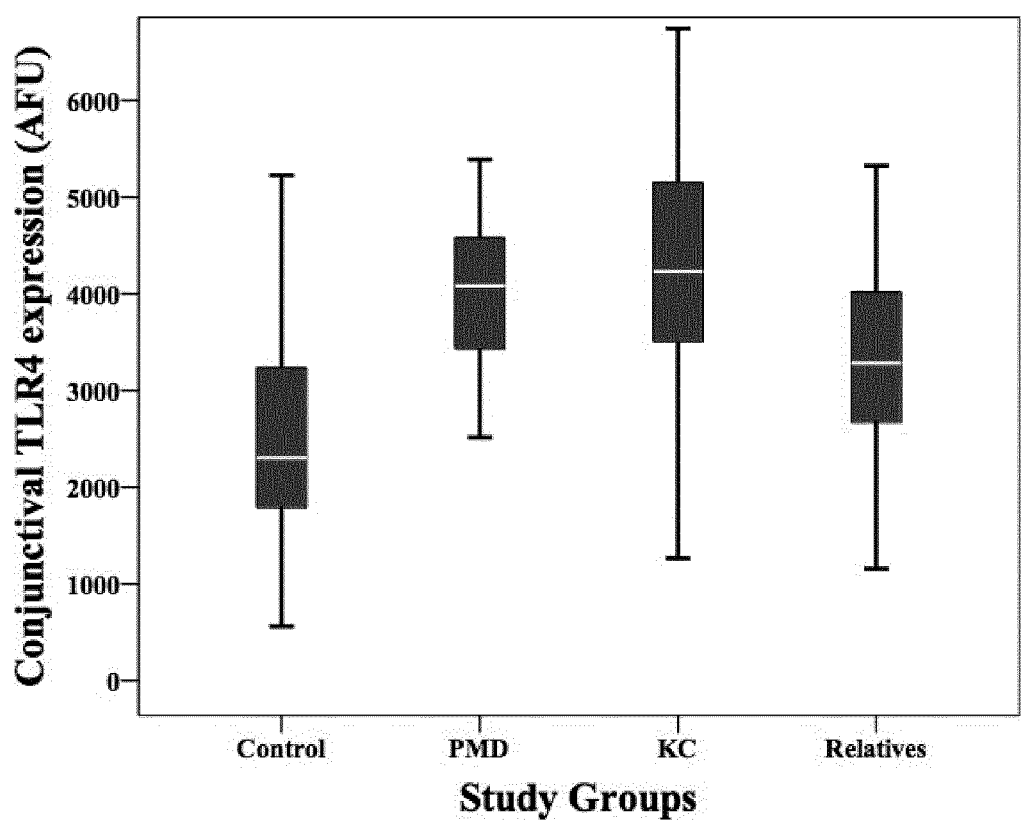
FIG. 5: Median [quartiles] of TLR4 expression levels in conjunctival cells by study groups in cohort B. A gradual increase in the expression of TLR4 is observed: Control<Relatives<pellucid marginal degeneration. However, keratoconus (KC) patients showed a similar expression of TLR4 in conjunctival cells than pellucid marginal degeneration (PMD) patients.

The inventors of the present invention have discovered that the ectasia process is related with the immunity response. In this regard, the inventors have shown that, unexpectedly, the expression levels of TLR2 and TLR4 proteins are increased in subjects diagnosed with an ectasia such as keratoconus or pellucid marginal degeneration. Moreover, the inventors of the present patent application have shown a correlation between increased expression level of TLR2 and TLR4 and certain parameters which are associated with progression of said disease. Thus, this allows the use of TLR2 and TLR4 not only as diagnostic markers of the disease, but also as surrogate markers to predict the risk of onset and progression of the disease.

Based on these findings, the inventors have developed the methods of the present invention in their different embodiments that will be described now in detail.

Method for Diagnosing Corneal Ectasia in a Subject

In a first aspect, the invention relates to an in vitro method for diagnosing an ectatic disease of the cornea in a subject, hereinafter, "the first method of the invention", which comprises:
    a) determining the expression level of TLR2 and/or TLR4 in a sample from said subject; and
    b) comparing said expression level with a reference value wherein, if the expression level of TLR2 and/or TLR4 is higher than said reference value is indicative that the subject suffers from an ectatic disease of the cornea.

The term "diagnosis" as used herein, refers both to the process of attempting to determine and/or identify a possible disease in a subject, i.e. the diagnostic procedure, and to the opinion reached by this process, i.e. the diagnostic opinion. As such, it can also be regarded as an attempt at classification of an individual's condition into separate and distinct categories that allow medical decisions about treatment and prognosis to be made. As the person skilled in the art will understand, such a diagnosis may not be correct for 100% of the subject to diagnose, although preferred it is. The term however requires that can identify a statistically significant proportion of subject suffering from such pathologies (in this case, corneal ectasia). The skilled in the art may determine whether a party is statistically significant using different statistical evaluation tools well known, for example, by determination of confidence intervals, the p-value determination, Student's-test, the Mann-Whitney, etc. Preferred confidence intervals are at least, 50%, at least 60%, at least 70%, at least 80%, at least 90% or at least 95%. The p-values are preferably, 0.05, 0.025, 0.001 or lower.

The term "ectatic disease of the cornea" or "corneal ectasia" as used herein, refers to a condition which involves the progressive thinning of the corneal thickness, thus affecting the structural integrity thereof giving rise to an alteration of the corneal curvature. The weakened cornea bulges, and crippling irregular astigmatism starts to develop. Corneal ectasia includes keratoconus, (which can be classified in subclinical keratoconus and clinical keratoconus), pellucid marginal degeneration, keratoglobus and ectasia post-refractive corneal surgery.

The curvature of the cornea can be determined by means of corneal topography methods such as videokeratography which allows determining several parameters related to corneal curvature such:
    K1: determines the curvature power of the flat meridian of the anterior surface of the cornea measured within the central 3 mm zone and expressed in diopters (D);
    K2: determines the curvature power of the steep meridian of the anterior surface of the cornea measured within the central 3 mm zone and expressed in diopters (D);
    Kc: determines maximum diopter power of the apex.
    Km: determines the mean curvature power of the anterior surface of the cornea within the central 3 mm zone expressed in diopters (D);
    Kmax: determines the maximum curvature power of the whole anterior surface of the cornea expressed in diopters (D);
    Thinnest location: determines the thickness area and the location of the thinnest point of the cornea (µm).
    Posterior corneal elevation (µm).

Said parameters measured in healthy subjects can be summarized as: K1 (central diopters) between 41.8 and 45.3 D; K2 between 42.2 and 45.3 D; posterior elevation between 0.024-0.036 µm; minimum thickness point between 513.5-567 µm.

In a particular embodiment, the first method of the invention relates to a method for diagnosing an ectatic disease of the cornea, wherein the ectatic disease of the cornea is selected from the group consisting of subclinical keratoconus, clinical keratoconus, pellucid marginal degeneration and postrefractive corneal ectasia.

The term "keratoconus" as used herein refers to a progressive disease of the cornea causing poor vision, in which the cornea adopts an irregular conical shape due to collagen fiber alteration in its internal structure. It is bilateral in most cases and progression is asymmetrical. The main anatomical symptom of keratoconus is the thinning in the central or paracentral area. i.e., the cornea becomes thinner as keratoconus develops, which leads to vision deterioration as keratoconus progresses. Keratoconus can be classified according to the videokeratographic guidelines proposed by Rabinowitz & McDonnell, it is possible to classify an eye as "subclinical keratoconus" if the simulated central corneal power is greater than 47.2 D but less than 48.7 D, with an inferior-superior dioptric asymmetry greater than 1.4 D, but less than 1.9 D. Eyes presenting central corneal curvature exceeding 48.7 D, as well as inferior-superior dioptric asymmetry greater than 1.9 D can be classified as "clinical keratoconus"; 2) The distance visual acuity (DVA) of the subclinical KC eye with value of 1.0 (without correction or with spherical and/or cylindrical compensation<1.50 D).

The term "pellucid marginal degeneration" or "PMD" as used herein refers to a degenerative corneal condition characterized by a clear bilateral thinning in the inferior and peripheral region of the cornea although some cases affect only one eye. Unlike keratoconus pain is not typically present in pellucid marginal degeneration, and aside from vision loss, no symptoms accompany the condition. However, in rare cases, PMD may present with sudden onset vision loss and excruciating eye pain, which occurs if the thinning of the cornea leads to perforation. Normally, PMD does not present with vascularization of the cornea, scarring, or any deposits of lipid.

The term "keratoglobus" as used herein refers to a degenerative non-inflammatory disorder of the eye in which structural changes within the cornea cause it to become extremely thin and change to a more globular shape than its normal gradual curve. It causes corneal thinning, primarily at the margins, resulting in a spherical, slightly enlarged eye.

The term "ectasia post refractive corneal surgery" as used herein refers to a condition due to the weakening of the inner layer of the cornea which occurs during surgery. It results in blurred and distorted vision due to increased myopia and astigmatism.

The term "TLR2" or "Toll-like receptor 2" as used herein, refers to a protein that in humans is encoded by the TLR2 gene. TLR2 has also been designated as CD282 (cluster of differentiation 282). TLR2 is one of the toll-like receptors and plays a role in the immune system. In particular, the sequence of human TLR2 protein is provided in the NCBI database entry NP_003255 (version of 25 May 2014).

The term "TLR4" or Toll-like receptor 2" as used herein, refers to a protein that in humans is encoded by the TLR4 gene. TLR 4 has also been designated as CD284 (cluster of differentiation 284). The molecular weight of TLR 4 is approximately 95 kDa. In particular, the sequence of human TLR4 protein is provided in the NCBI database entry NP_003257 (version of 25 May 2014).

The term "subject", as used herein, refers to all animals classified as mammals and includes, but is not restricted to, domestic and farm animals, primates and humans, e.g., human beings, non-human primates, cows, horses, pigs, sheep, goats, dogs, cats, or rodents. Preferably, the patient is a male or female human of any age or race.

In the present invention, the term "sample" or "biological sample" means biological material isolated from a subject's eye. The biological sample can contain any biological material suitable for detecting the desired biomarker and can comprise cell and/or non-cell material of the subject. In a preferred embodiment, the sample is any sample which contains cells from the cornea tissue. In another preferred embodiment, the sample is any sample which contains cells from the conjunctiva tissue. The sample can be isolated by using any conventional method known in the art. Briefly, corneal epithelial cells may be obtained from a subject by mechanical debridement using a sterile corneal scraper, by impression cytology or by harvesting cells which are suspended tear samples, such as corneal epithelial cells released into the tear film by rubbing the eyes and collected with micropipettes using standard techniques, or by any other technique known. Where the sample are conjunctive cells from the conjunctive tissue, they can be obtained using know sampling techniques such as tissue sampled using a micro trephine.

In a preferred embodiment, the first method of the invention comprises determining the expression level of TLR2 in a sample from the subject to be diagnosed.

In another preferred embodiment, the first method of the invention comprises determining the expression level of TLR4 in a sample from the subject to be diagnosed.

In another preferred embodiment, the first method of the invention comprises determining the expression level of TLR2 and TLR4 in a sample from the subject to be diagnosed.

As it is used herein, the term "expression level" refers to the value of a parameter that measures the degree of expression of a specific gene or of the corresponding polypeptide. In a particular embodiment, said value can be determined by measuring the mRNA level of the gene of interest or a fragment thereof or by measuring the amount of protein encoded by said gene of interest or a variant thereof. Thus, in the context of the present invention, in a particular embodiment, said expression level comprises determining the level of the mRNA encoded from the TLR2 and/or TLR4 gene or determining the level of the TLR2 and/or TLR4 protein.

Virtually any conventional method for detecting and quantifying the expression level of a gene can be used within the framework of the present invention for detecting and quantifying the expression level of a specific gene. By way of non-limiting illustration, the expression level of a gene can be determined by means of quantifying the mRNA level of said gene or by means of quantifying the level of protein encoded by said gene. Methods for determining the amount of mRNA are well-known in the state of the art. For example, the nucleic acid contained in the sample, such as the eye's sample from the subject under study, is extracted according to conventional methods, for example, by means of using lytic enzymes, chemical solutions or fixing resins. The extracted mRNA can be detected by hybridization (for example by means of Northern blot analysis or DNA or RNA arrays (microarrays) after converting mRNA into labeled cDNA) and/or amplification by means of a enzymatic chain reaction. In general, quantitative or semi-quantitative enzymatic amplification methods are preferred. The polymerase chain reaction (PCR) or quantitative real-time RT-PCR or semi-quantitative RT-PCR technique is particularly advantageous. Primer pairs are preferably designed for the purpose of superimposing an intron to distinguish cDNA amplification from the contamination from genomic DNA (gDNA). Additional primers or probes, which are preferably labeled, for example with fluorescence, which hybridize specifically in regions located between two exons, are optionally designed for the purpose of distinguishing cDNA amplification from the contamination from gDNA. If desired, said primers can be designed such that approximately the nucleotides comprised from the 5' end to half the total length of the primer hybridize with one of the exons of interest, and approximately the nucleotides comprised from the 3' end to half the total length of said primer hybridize with the other exon of interest. Suitable primers can be readily designed by a person skilled in the art. Other amplification methods include ligase chain reaction (LCR), transcription-mediated amplification (TMA), strand displacement amplification (SDA) and nucleic acid sequence based amplification (NASBA). The amount of mRNA is preferably measured quantitatively or semi-quantitatively. Relevant information about conventional methods for quantifying the expression level of a gene can be found, for example, in Sambrook et al., 2001 [Sambrook, J., et al., "Molecular cloning: a Laboratory Manual", 3rd ed., Cold Spring Harbor Laboratory Press, N.Y., Vol. 1-3].

To normalize the expression values of one gene among different samples, comparing the mRNA level of the gene of interest (i.e. TLR2 and/or TLR4) in the samples from the subject object of study with a control RNA level is possible. As it is used herein, a "control RNA" is RNA of a gene the expression level of which does not differ depending on if the subject suffers from an ectatic disease of the cornea or not; a control RNA is preferably an mRNA derived from a housekeeping gene encoding a protein that is constitutively expressed and carrying out essential cell functions. Illustrative, non-limiting examples of housekeeping genes for use in the present invention include GUSB (beta-glucuronidase), PPIA (peptidyl-prolyl isomerase A), β-2-microglobulin, GAPDH, PSMB4 (proteasome subunit beta type-4), ubiquitin, transferrin receptor, 18-S ribosomal RNA, cyclophilin, tubulin, β-actin, 3-monooxygenase/tryptophan 5-monooxygenase tyrosine activation protein (YWHAZ), etc. If the expression level of TLR2 and/or TLR4 is determined by measuring the expression level of transcription product (mRNA) of said gene in a sample from the subject under study, the sample can be treated to physically or mechanically break up the structure of the tissue or cell for the purpose of releasing the intracellular components into an aqueous or organic solution to prepare the nucleic acids for additional analysis. Care is preferably taken to prevent RNA degradation during the extraction process.

In a particular and preferred embodiment of the invention, the expression level of TLR2 is determined by means of determining the expression level of the protein encoded by the TLR2 gene or a variant thereof, because increased expression of a gene is usually accompanied by an increase in the amount of corresponding protein, is also possible. The term "variant" as used herein, relates to those variant of human TLR2 which appear naturally in other species, i.e. the orthologues of TLR2. Said variants include, without limitation, mouse TLR2, which corresponds to the sequence with accession number NP_036035 dated 25 May 2014 in the NCBI database; pig TLR2, which corresponds to the sequence with accession number NP_998926 dated 10 Jan. 2014 in the NCBI database; macaque TLR2, which corresponds to the sequence with accession number NP_001123897 dated 2 Mar. 2014 in the NCBI database; rat TLR2, which corresponds to the sequence with accession number NP_942064 dated 10 Aug. 2014 in the NCBI database.

In another particular and preferred embodiment of the invention, the expression level of TLR4 is determined by means of determining the expression level of the protein encoded by the TLR4 gene or a variant thereof. Said variants include, without limitation, mouse TLR4, which corresponds to the sequence with accession number NP_067272 dated 4 May 2014 in the NCBI database; pig TLR4, which corresponds to the sequence with accession number NP_001280245 dated 7 Jun. 2014 in the NCBI database; macaque TLR4, which corresponds to the sequence with accession number NP_001032169 dated 26 Feb. 2014 in the NCBI database; rat TLR4, which corresponds to the sequence with accession number NP_062051 dated 10 Aug. 2014 in the NCBI database.

The natural variants of TLR2 and/or TLR4 suitable for their use in the present invention also derive from said sequence by insertion, substitution or deletion of one or more amino acids and include natural alleles, variants resulting from alternative processing and truncate forms which appear naturally. The term "variant" also includes fragments, isoforms and analogues or derivatives of TLR2 and/or TLR4. Preferably, variants of TLR2 and/or TLR4 are (i) polypeptides in which one or more amino acid residues are substituted by a preserved or non-preserved amino acid residue (preferably a preserved amino acid residue) and such substituted amino acid may be coded or not by the genetic code, (ii) polypeptides in which there is one or more modified amino acid residues, for example, residues modified by substituent bonding, (iii) polypeptides resulting from alternative processing of a similar mRNA, (iv) polypeptide fragments and/or (iv) polypeptides resulting from TLR2 and/or TLR4 fusion or the polypeptide defined in (i) to (iii) with another polypeptide, such as a secretory leader sequence or a sequence being used for purification (for example, His tag) or for detection (for example, Sv5 epitope tag). The fragments include polypeptides generated through proteolytic cut (including multisite proteolysis) of an original sequence. The variants may be post-translationally or chemically modified. Such variants are supposed to be apparent to those skilled in the art.

Variants according to the present invention includes amino acid sequences that are at least 60%, 65%, 70%, 72%, 74%, 76%, 78%, 80%, 90%, or 95% similar or identical to the original amino acid sequence. The degree of identity between two proteins is determined using computer algorithms and methods that are widely known for the persons skilled in the art. The identity between two amino acid sequences is preferably determined by using the BLASTP algorithm [BLASTManual, Altschul, S., et al., NCBI NLM NIH Bethesda, Md. 20894, Altschul, S., et al., J. Mol. Biol. 215: 403-410 (1990)].

The proteins can be post-translationally modified. For example, post-translational modifications that fall within the scope of the present invention include signal peptide cleavage, glycosylation, acetylation, isoprenylation, proteolysis myristoylation, protein folding and proteolytic processing, etc. Additionally, the proteins may include unnatural amino acids formed by post-translational modification or by introducing unnatural amino acids during translation.

The determination of the amount of a protein corresponding to the expression of a specific gene can be performed using any conventional method for protein detection and quantification, for example by means of an immunoassay, etc. By way of non-limiting illustration, said determination can be performed using antibodies with the capability to bind specifically to the protein to be determined (or fragments thereof with the antigenic determinants) and subsequent quantification of the antigen-antibody complex derivatives. The antibodies can be, for example, polyclonal sera, hybridoma supernatants or monoclonal antibodies, fragments of antibodies, Fv, Fab, Fab' and F(ab')$_2$, scFv, diabodies, triabodies, tetrabodies, humanized antibodies, etc. Said antibodies may (or may not) be labeled with a marker. Illustrative, non-limiting examples of markers that can be used in the present invention include radioactive isotopes, enzymes, fluorophores, chemiluminescent reagents, enzyme cofactors, enzyme substrates, enzyme inhibitors, etc. There is a wide range of well-known assays that can be used in the present invention, such as, for example, assays based on Western-blot or immunoblot techniques, ELISA (enzyme-linked immunosorbent assay), RIA (radioimmunoassay), EIA (enzyme immunoassay), DAS-ELISA (double antibody sandwich ELISA), immunocytochemical or immunohistochemical techniques such as flow cytometry, etc. Other ways of detecting and quantifying the protein include affinity chromatography, ligand binding assay techniques, particle-enhanced turbidimetric immunoassay (PETIA) etc.

In a particular embodiment, the determination of the expression level of the TLR2 and/or TLR4 protein is carried out by immunohistochemistry or ELISA or protein array. In a preferred embodiment, the expression level of TLR2 and/or TLR4 is determined by flow cytometry. Briefly, flow cytometry, is a laser-based biophysical technology which allows simultaneous multiparametric analysis of the physical and chemical characteristics of up to thousands particles per second. Is based in using fluorescent labels or fluorophores which are typically attached to an antibody that recognizes a target feature on or in the cell; they may also be attached to a chemical entity with affinity for the cell membrane or another cellular structure. Each fluorophore has characteristic peak excitation and emission wavelength, and the emission spectra often overlap. Consequently, the combination of labels which can be used depends on the wavelength of the lamp(s) or laser(s) used to excite the fluorochromes and on the detectors available.

If desired, to normalize the expression values of one protein, i.e. TLR2 and/or TLR4, among different samples, comparing the protein level of the protein of interest in the samples from the subject object of study with a control protein level is possible. In one particular embodiment, the expression level of TLR2 and/or TLR4 is determined in absolute terms, i.e. by providing the concentration of TLR2 and/or TLR4 in a sample. In another particular embodiment, the expression level of TLR2 and/or TLR4 is measured relative to total protein amount in a sample.

The second step of the first method of the invention comprises comparing the expression level of TLR2 and/or TLR4 obtained in the first step of said method with a reference value. The term "reference value" as used herein, refers to a laboratory value used as a reference for the values/data obtained from samples obtained from the subjects. The reference value (or reference level) can be an absolute value, a relative value, a value which has an upper and/or lower limit, a series of values, an average value, a median, a mean value, or a value expressed by reference to a control or reference value. A reference value can be based on the value obtained from an individual sample, such as, for example, a value obtained from a sample from the subject object of study but obtained at a previous point in time. The reference value can be based on a high number of samples, such as the values obtained in a population of the subjects of the chronological age group coinciding with that of the subject object of study or based on a set of inclusion or exclusion samples of the sample to be analyzed. The reference value can be based on the expression values of the marker to be compared obtained from samples from healthy subjects who do not have a disease state or a particular phenotype. For example, the reference value can be based on the expression level of the marker to be analyzed obtained from subjects who do not have corneal ectasia, preferably from healthy subjects without suffering from any corneal trauma or corneal-conjunctival disease or any ocular disease. In a preferred embodiment, the reference value is obtained from a sample or a set of samples from healthy subjects or subjects without prior history corneal ectasia.

The reference value can also be based on the expression values of the marker to be compared obtained from samples from subjects having a particular phenotype.

Once the reference value has been established, the expression level of TLR2 and/or TLR4 in the sample from the subject under study is compared with the reference value. As a consequence of this comparison, the expression level of the marker of interest (for example, TLR2 and/or TLR4 in the first method of the invention) in the sample from the subject can be "greater than", "less than" or "equal to" said reference value for said gene. In the context of the present invention, it is considered that an expression level of TLR2 and/or TLR4 in the sample from the subject is "greater than" or "higher than" the reference value for said marker when the expression level of TLR2 and/or TLR4 in the sample from the subject increases, for example, 5%, 10%, 25%, 50%, 100% or even more when compared with the reference value for said gene, or when it increases, for example, at least 1.1-fold, 1.5-fold, 2-fold, 5-fold, 10-fold, 20-fold, 30-fold, 40-fold, 50-fold, 60-fold, 70-fold, 80-fold, 90-fold, 100-fold or even more when compared with the reference value for said marker. In the context of the present invention, it is also considered that an expression level of the marker of interest (for example, TLR2 and/or TLR4 in the first method of the invention) in the sample from the subject is "less than" the reference value for said marker when the expression level of TLR2 and/or TLR4 in the sample from the subject decreases, for example, 5%, 10%, 25%, 50%, 75%, or even 100% when compared with the reference value for said marker.

In the context of the present invention, it is also considered that an expression level of the marker of interest (i.e. TLR2 and/or TLR4 in the first method of the invention) in the sample from the subject is "equal to" the reference value for said marker when the expression level of TLR2 and/or TLR4 is substantially unchanged with respect to the reference value; for example, it is considered that the expression level of TLR2 and/or TLR4 in the sample from the subject under study is "equal to" the reference value when the levels differ by not more than 0.1%, not more than 0.2%, not more than 0.3%, not more than 0.4%, not more than 0.5%, not more than 0.6%, not more than 0.7%, not more than 0.8%, not more than 0.9%, not more than 1%, not more than 2%, not more than 3%, not more than 4%, not more than 5%, or not more than the percentage value which is the same as the error associated with the experimental method used in the determination.

Once the comparison is made between the expression level of TLR2 and/or TLR4 in the sample from the subject and the reference value for said marker, the first method of the invention allows determining if a subject suffers from an ectatic disease of the cornea based on if the expression level of TLR2 and/or TLR4 is higher than said reference value.

In a particular embodiment of the first method of the invention, is aimed at diagnosing a subject as suffering from subclinical keratoconus, in which case the reference value corresponds to the expression levels of TLR2 and/or TLR4 measured in a sample from a subject from a healthy subject, preferably from subjects who do not have corneal ectasia, preferably from healthy subjects without suffering from any corneal trauma or corneal-conjunctival disease or any ocular disease. In a preferred embodiment, the reference value is obtained from a sample or a set of samples from healthy subjects or subjects without prior history corneal ectasia. In this particular embodiment, once the comparison is made between the expression level of TLR2 and/or TLR4 in the sample from the subject and the reference value for said marker, the first method of the invention allows determining if a subject suffers from subclinical keratoconus based on if the expression level of TLR2 and/or TLR4 is higher than said reference value. As it is shown in the Examples of the present application, values of TLR2 measured by flow cytometry in the conjunctive tissue of healthy subjects are about 213 (90-295) AUF (Arbitrary Fluorescence Units); values of TLR2 measured by flow cytometry in the corneal tissue of healthy subjects are about 185 (113-286) AUF; values of TLR4 measured by flow cytometry in the conjunctive tissue of healthy subjects are about 1581 (1281-2265) AUF (Arbitrary Fluorescence Units); values of TLR4 measured by flow cytometry in the corneal tissue of healthy subjects are about 1654 (1134-2587) AUF. Therefore, if desired, said values can be used as the reference value in the second step of the first method of the invention.

In another particular embodiment, the first method of the invention is aimed at diagnosing a subject as suffering from clinical keratoconus, in which case the reference value corresponds to the expression levels of TLR2 and/or TLR4 measured in a sample from a subject suffering from subclinical keratoconus. In this particular embodiment, once the comparison is made between the expression level of TLR2 and/or TLR4 in the sample from the subject and the reference value for said marker, the first method of the invention allows determining if a subject suffers from clinical keratoconus based on if the expression level of TLR2 and/or TLR4 is higher than said reference value. As it is shown in the Examples of the present application, values of TLR2 measured by flow cytometry in the conjunctive tissue of subjects suffering from subclinical keratoconus are about 207 (124-398) AUF; values of TLR2 measured by flow cytometry in the corneal tissue of subjects suffering from subclinical keratoconus are about 977 (647-1330) AUF; values of TLR4 measured by flow cytometry in the conjunctive tissue of subjects suffering from subclinical keratoconus are about 1922 (1574-2778) AUF (Arbitrary Fluorescence Units); values of TLR4 measured by flow cytometry in the corneal tissue of subjects suffering from subclinical keratoconus are about 2569 (2071-3808) AUF. Therefore, if desired, said values can be used as the reference value in the second step of the first method of the invention.

In yet another particular embodiment, the first method of the invention is aimed at diagnosing a subject as suffering from pellucid marginal degeneration, in which case the reference value corresponds to the expression levels of TLR2 and/or TLR4 measured in a sample from a healthy subject. In this particular embodiment, once the comparison is made between the expression level of TLR2 and/or TLR4 in the sample from the subject and the reference value for said marker, the first method of the invention allows determining if a subject suffers from pellucid marginal degeneration based on if the expression level of TLR2 and/or TLR4 is higher than said reference value. As it is shown in the Examples of the present application, values of TLR2 measured by flow cytometry in the conjunctive tissue of healthy subjects are about 733 (560-946) AUF; values of TLR2 measured by flow cytometry in the corneal tissue of healthy subjects are about 580 (413-976) AUF; values of TLR4 measured by flow cytometry in the conjunctive tissue of healthy subjects are about 2380 (1781-3283) AUF (Arbitrary Fluorescence Units); values of TLR4 measured by flow cytometry in the corneal tissue of healthy subjects are about 1572 (949-2353) AUF. Therefore, if desired, said values can be used as the reference value in the second step of the first method of the invention. In a particular embodiment, the first method of the invention is aimed at diagnosing a subject as suffering from pellucid marginal degeneration if the expression level of TLR2 in corneal tissue is higher than said reference value.

In another particular embodiment, the first method of the invention is aimed at diagnosing a subject as suffering from pellucid marginal degeneration if the expression level of TLR4 in corneal or conjunctival tissue is higher than said reference value, preferably in conjunctival tissue.

In another particular embodiment, the first method of the invention also comprises determining at least one parameter selected from: diopters, corneal thickness and corneal elevation.

The term "diopter" as used herein refers to a unit of magnifying power of a lens or lens system. Because the power of a lens is proportional to unity (one) divided by the focal length, the power of a lens in diopters is numerically equal to 1 m divided by the focal length in meters. The algebraic signs of the magnifying power indicate whether the lens causes an incident pencil of parallel light rays to converge or to diverge. Thus, diverging lens having a focal length of 1 m has a power of −1 diopter. The diopter can also be used as a measurement of curvature equal to the reciprocal of the radius measured in meters.

Method for Determining the Risk of Developing an Ectatic Disease of the Cornea in a Subject In a second aspect, the invention relates to an in vitro method for determining the risk of developing an ectatic disease of the cornea in a subject, hereinafter, "the second method of the invention" which comprises:
  a) determining the expression level of TLR2 and/or TLR4 in a sample from said subject; and
  b) comparing said expression level with a reference value wherein, if the expression level of TLR2 and/or TLR4 is higher than said reference value is indicative that the subject has high risk of developing an ectatic disease of the cornea.

The expression "determining the risk" or "prediction of the risk", or similar, as used herein, is synonymous of the expression "assessing the risk" or "assessment of the risk", means that the present invention makes it possible to predict, estimate or evaluate the risk of a subject to developing an ectatic disease of the cornea. The prediction of risk generally implies that the risk is either increased or reduced. As it will be understood by those skilled in the art, the prediction (or the risk), although preferred to be, need not be correct for 100% of the patients suffering ectatic diseases of the cornea to be evaluated. The term, however, requires that a statistically significant portion subjects can be identified as having an increased probability of having an ectatic disease of the cornea. Whether a subject is statistically significant can be determined without further ado by the person skilled in the art by using various well known statistic evaluation tools, e.g., determination of confidence intervals, p-value determination, Student's t-test, Mann-Whitney test, etc. Details can be found in Dowdy and Wearden, Statistics for Research, John Wiley & Sons, New York 1983. Preferred confidence intervals are at least 50%, at least 60%, at least 70%, at least 80%, at least 90% at least 95%. The p-values are, preferably 0.05, 0.025, 0.001, 0.0001 or lower.

The second method of the invention comprises determining the expression level of TLR2 and/or TLR4 in a sample from said subject.

In a preferred embodiment, the second method of the invention comprises determining the expression level of TLR2 in a sample from the subject under study.

In another preferred embodiment, the second method of the invention comprises determining the expression level of TLR4 in a sample from the subject under study.

In another preferred embodiment, the second method of the invention comprises determining the expression level of TLR2 and TLR4 in a sample from the subject under study.

The terms "subject", "sample" and "ectatic disease of the cornea" have been previously defined in the context of the first method of the invention and are equally applicable to the second method of the invention.

In a particular embodiment, the sample from said subject is selected from conjunctival and corneal tissue. Methods for obtaining samples from conjunctival and corneal tissues have been detailed in the first method of the invention.

In another particular embodiment, the ectatic disease is selected from subclinical keratoconus, clinical keratoconus, pellucid margin degeneration, keratoglobus and ectasia post-refractive corneal surgery. The terms "subclinical keratoconus", "clinical keratoconus", "pellucid margin degeneration", "keratoglobus" and "ectasia post-refractive corneal surgery" have been previously defined.

The terms "TLR2", "TLR4" and "expression level" have been previously defined. In a particular embodiment, said expression level comprises determining the level of mRNA encoded from the TLR2 and/or TLR4 gene or determining the level of the TLR2 and/or TLR4 protein. Methods for determining the expression levels of TLR2 and/or TLR2 have been detailed in the context of the first method of the invention and are equally applicable to the second method of the invention.

In a particular embodiment, the determination of the expression level of the TLR2 and/or TLR4 protein is carried out by immunohistochemistry or ELISA or protein array. In a preferred embodiment, the expression level of TLR2 and/or TLR4 is determined by flow cytometry.

The second step of the second method of the invention comprises comparing the expression levels of TLR2 and/or TLR4 with a reference value. The term "reference value" has been previously defined in the context of the first method of the invention.

Once the comparison is made between the expression level of TLR2 and/or TLR4 in the sample from the subject under study and the reference value, the second method of the invention allows determining if a subject has a high risk of developing an ectatic disease of the cornea based on if the expression level of TLR2 and/or TLR4 is higher than said reference value. The terms "higher than", "less than" and "equal to" have been previously defined.

In a particular embodiment, the second method of the invention is aimed at determining the risk of developing an ectatic disease of the cornea in a subject previously diagnosed as having a refractive defect.

The term "refractive defect" as used herein refers to an error in the focusing of light by the eye on the retina. Refractive defects include:
  myopia which refers to a refractive defect in the eye in which parallel rays of light from a distance converge at a focal point located in front of the retina instead of the retina itself, as it normally would;
  astigmatism which refers to an eye defect which is characterized by a different refraction between two meridians of the eye, which prevents clearly focusing on objects and is generally due to an impairment in the front curvature of the cornea;
  hyperopia (or hypermetropia) which is a defect of vision caused by an imperfection of the eye (often when the eyeball is too short or the lens cannot become round enough), causing difficulty focusing on near objects;
  presbyopia which is a condition associated with aging in which the eye exhibits a progressively diminished ability to focus near objects.

In a preferred embodiment, the subject has been previously diagnosed as having subclinical keratoconus (simulated central corneal power is greater than 47.2 D but less than 48.7 D, with an inferior-superior dioptric asymmetry greater than 1.4 D, but less than 1.9 D).

In another particular embodiment of the invention, the subject under study has developed a previous ocular pathology selected from: ocular itching, eye rubbing, biomicroscopic signs and conjunctival hyperemia.

The term "ocular itching" as used herein refers to ocular pruritus which may be caused by atopic keratoconjunctivitis, vernal keratoconjunctivitis allergic conjunctivitis and atopic dermatitis among others. Other causes include dry eye syndrome, meibomian gland dysfunction, blepharithis, contact-lens induced conjunctivitis, giant papillary conjunctivitis and contact dermatoblepharithis.

The term "biomicroscopic signs" as used herein, refers to abnormalities in the areas at the front of the eye, including the eyelids, conjunctiva, iris, lens, sclera, and cornea. The retina and optic nerve can also be seen.

The term "conjunctival hyperemia" as used herein refers to an engorgement of the blood vessels in the conjunctiva due to an inflammation reaction.

Method for Determining the Clinical Outcome of a Subject Suffering from an Ectatic Disease of the Cornea In a third aspect, the invention relates to an in vitro method for determining the clinical outcome of a subject suffering from an ectatic disease of the cornea, hereinafter, "the third method of the invention" which comprises:
  a) determining the expression level of TLR2 and/or TLR4 in a sample from said subject; and
  b) comparing said expression level with a reference value
  wherein, if the expression level of TLR2 and/or TLR4 is higher than said reference value is indicative of a negative clinical outcome.

The term "determining the outcome" or "predicting the outcome", is used herein to refer to the likelihood that a patient will have a particular clinical outcome, whether positive or negative. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as refractive surgery. The prediction may include prognostic factors.

As will be understood by those skilled in the art, the prediction, although preferred to be, need not be correct for 100% of the subjects to be evaluated. The term, however, requires that a statistically significant portion of subjects can be identified as having an increased probability of having a given outcome. Whether a subject is statistically significant can be determined without further ado by the person skilled in the art using various well known statistic evaluation tools, e.g., determination of confidence intervals, p-value determination, cross-validated classification rates and the like etc. Details are found in Dowdy and Wearden, Statistics for Research, John Wiley & Sons, New York 1983. Preferred confidence intervals are at least 50%, at least 60%, at least 70%, at least 80%, at least 90% or at least 95%. The p-values are, preferably, 0.01, 0.005 or lower.

The third method of the invention comprises determining the expression level of TLR2 and/or TLR4 in a sample from said subject.

In a preferred embodiment, the third method of the invention comprises determining the expression level of TLR2 in a sample from the subject under study.

In another preferred embodiment, the third method of the invention comprises determining the expression level of TLR4 in a sample from the subject under study.

In another preferred embodiment, the third method of the invention comprises determining the expression level of TLR2 and TLR4 in a sample from the subject under study.

The first step of the third method of the invention comprises determining the expression levels of TLR2 and/or TLR4 in a sample for the subject under study.

The terms "subject", "sample" and "ectatic disease of the cornea" have been previously defined in the context of the first method of the invention and are equally applicable to the third method of the invention.

In a particular embodiment, the sample from said subject is selected from conjunctival and corneal tissue. Methods for obtaining samples from conjunctival and corneal tissues have been detailed in the first method of the invention.

In another particular embodiment, the ectatic disease is selected from subclinical keratoconus, clinical keratoconus, pellucid margin degeneration, keratoglobus and ectasia post refractive corneal surgery. The terms "subclinical keratoconus", "clinical keratoconus", "pellucid margin degeneration", "keratoglobus" and "ectasia post refractive corneal surgery" have been previously defined.

The terms "TLR2", "TLR4" and "expression level" have been previously defined. In a particular embodiment, said expression level comprises determining the level of mRNA encoded from the TLR2 and/or TLR4 gene or determining the level of the TLR2 and/or TLR4 protein. Methods for determining the expression levels of TLR2 and/or TLR2 have been detailed in the context of the first method of the invention and are equally applicable to the third method of the invention.

In a particular embodiment, the determination of the expression level of the TLR2 and/or TLR4 protein is carried out by immunohistochemistry or ELISA or protein array. In a preferred embodiment, the expression level of TLR2 and/or TLR4 is determined by flow cytometry.

The second step of the third method of the invention comprises comparing the expression levels of TLR2 and/or TLR4 with a reference value. The term "reference value" has been previously defined. In a particular embodiment, said reference value is obtained from a sample or a set of samples from healthy subjects or subjects without prior history corneal ectasia.

In another particular embodiment, said reference value refers to the TLR2 and/or TLR4 expression levels in a sample from said subject obtained at earlier point of time. Thus, according to the third method of the invention, the expression levels of TLR2 and/or TLR4 determined in a sample from a subject suffering from an ectatic disease of the cornea obtained at first time are compared with the expression levels of TLR2 and/or TLR4 determined in a sample from a subject suffering from an ectatic disease of the cornea obtained at a second period of time. The second subjects sample can be taken at any time after the first period of time, e.g., one day, one week, one month, two months, three months, six months 1 year, 2 years, 5 years, 10 years or more after the first subject sample.

Lastly, the subject is then classified as having a negative outcome if the expression level of TLR2 and/or TLR4 is higher than said expression levels in the reference sample.

The term "positive outcome" in relation to ectatic disease of the cornea means that the degeneration of the cornea does not advance. Said term also encompass a decrease in the cornea degeneration rate.

The term "negative outcome" in relation to ectatic disease of the cornea means that the degeneration of the cornea progresses.

Method for Selecting a Subject to be Treated with a Therapy for an Ectatic Disease of the Cornea In a fourth aspect, the invention relates to an in vitro method for selecting a subject to be treated with a therapy for an ectatic disease of the cornea, hereinafter, "the fourth method of the invention" which comprises:

a) determining the expression level of TLR2 and/or TLR4 in a sample from said subject; and b) comparing said expression level with a reference value wherein, if the expression level of TLR2 and/or TLR4 is higher than said reference value is indicative that said subject is candidate to be treated with a therapy for ab ectatic disease of the cornea.

The term "selecting a subject for a therapy", as used herein, relates to the identification of a subject for a therapy designed to cure a disease or palliate the symptoms associated with one or more diseases or conditions. In the particular case of ectatic disease of the corneal therapy, it is understood any therapy which abolishes, retards or reduces the symptoms associated with corneal ectasia. Adequate therapies which can be used according to the invention to treat ectatic diseases of the cornea include corneal crosslinking, intracorneal rings and refractive surgery.

Corneal crosslinking is a technique which uses ultraviolet light or light in the blue spectrum and a photosensiziter to strengthen chemical bonds in the cornea and thereby increase the corneal stiffness.

Intrastromal corneal rings or intracorneal rings are small devices implanted in the eye to correct vision. A typical vision correction using corneal rings would involve an ophthalmologist making a small incision in the cornea of the eye and inserting two crescent or semi-circular shaped rings segments between the layers of the corneal stroma, one on each side of the pupil. The embedding of the rings in the cornea has the effect of flattening the cornea and changing the refraction of light passing through the cornea on its way into the eye.

The refractive eye surgery is used to improve the refractive state of the eye and decrease or eliminate dependency on glasses or contact lenses. This can include various methods of surgical remodeling of the cornea. The most common methods today, such as Automated Lamellar Keratoplasty (ALK), Laser-assisted in situ Keratomileusis (LASIK) or ReLEx, use excimer lasers to reshape the curvature of the cornea.

The fourth method of the invention comprises determining the expression level of TLR2 and/or TLR4 in a sample from said subject.

In a preferred embodiment, the fourth method of the invention comprises determining the expression level of TLR2 in a sample from the subject under study.

In another preferred embodiment, the fourth method of the invention comprises determining the expression level of TLR4 in a sample from the subject under study.

In another preferred embodiment, the fourth method of the invention comprises determining the expression level of TLR2 and TLR4 in a sample from the subject under study.

The first step of the fourth method of the invention comprises determining the expression levels of TLR2 and/or TLR4 in a sample for the subject under study.

The terms "subject", "sample" and "ectatic disease of the cornea" have been previously defined in the context of the first method of the invention and are equally applicable to the fourth method of the invention.

In a particular embodiment, the sample from said subject is selected from conjunctival and corneal tissue. Methods for obtaining samples from conjunctival and corneal tissues have been detailed in the first method of the invention.

In another particular embodiment, the ectatic disease is selected from subclinical keratoconus, clinical keratoconus, pellucid margin degeneration, keratoglobus and ectasia post refractive corneal surgery. The terms "subclinical keratoconus", "clinical keratoconus", "pellucid margin degeneration", "keratoglobus" and "ectasia post refractive corneal surgery" have been previously defined.

The terms "TLR2", "TLR4" and "expression level" have been previously defined. In a particular embodiment, said expression level comprises determining the level of mRNA encoded from the TLR2 and/or TLR4 gene or determining the level of the TLR2 and/or TLR4 protein. Methods for determining the expression levels of TLR2 and/or TLR2 have been detailed in the context of the first method of the invention and are equally applicable to the third method of the invention.

In a particular embodiment, the determination of the expression level of the TLR2 and/or TLR4 protein is carried out by immunohistochemistry or ELISA or protein array. In a preferred embodiment, the expression level of TLR2 and/or TLR4 is determined by flow cytometry.

The second step of the fourth method of the invention comprises comparing the expression levels of TLR2 and/or TLR4 with a reference value. The term "reference value" has been previously defined. In a particular embodiment, said reference value is obtained from a sample or a set of samples from healthy subjects or subjects without prior history corneal ectasia.

Once the comparison is made between the expression level of TLR2 and/or TLR4 in the sample from the subject under study and the reference value, the fourth method of the invention allows selecting a subject to be treated with a therapy for an ectatic disease of the cornea based on if the expression level of TLR2 and/or TLR4 is higher than said reference value. The terms "higher than", "less than" and "equal to" have been previously defined.

Method for Selecting a Refractive Surgery as Therapy for a Subject Suffering from a Refractive Defect In a fifth aspect, the invention relates to an in vitro method for determining whether a subject suffering from a refractive defect is a candidate for a refractive surgery therapy which comprises:
  a) determining the expression level of TLR2 and/or TLR4 in a sample from said subject; and
  b) comparing said expression level with a reference value wherein if the expression level of TLR2 and/or TLR4 is higher than said reference value is indicative that said subject is not candidate to be treated with a refractive surgery for said refractive defect.

In a preferred embodiment, the fifth method of the invention comprises determining the expression level of TLR2 and TLR4 in a sample from the subject under study.

The term "refractive surgery" as used herein refers to any eye surgery used to improve the refractive state of the eye based on remodeling the curvature of the cornea.

The first step of the fifth method of the invention comprises determining the expression levels of TLR2 and/or TLR4 in a sample for the subject under study.

The terms "subject", "sample" and "refractive defect" have been previously defined in the context of the first method of the invention and are equally applicable to the fifth method of the invention.

In a particular embodiment, the sample from said subject is selected from conjunctival and corneal tissue. Methods for obtaining samples from conjunctival and corneal tissues have been detailed in the first method of the invention.

In a particular embodiment, the determination of the expression level of the TLR2 and/or TLR4 protein is carried out by immunohistochemistry or ELISA or protein array. In a preferred embodiment, the expression level of TLR2 and/or TLR4 is determined by flow cytometry.

The second step of the fifth method of the invention comprises comparing the expression levels of TLR2 and/or TLR4 with a reference value. The term "reference value" has been previously defined.

Once the comparison is made between the expression level of TLR2 and/or TLR4 in the sample from the subject under study and the reference value, the fourth method of the invention allows selecting a subject to be treated with a therapy for an ectatic disease of the cornea based on if the expression level of TLR2 and/or TLR4 is higher than said reference value. The terms "higher than", "less than" and "equal to" have been previously defined.

Uses of the Invention

In a sixth aspect, the invention relates to the use of TLR2 and/or TLR4 as a marker for determining the diagnosis of an ectatic disease of the cornea.

In a seventh aspect, the invention relates to the use of TLR2 and/or TLR4 as a marker for determining the risk of developing an ectatic disease of the cornea in a subject.

In an eight aspect, the invention relates to the use of TLR2 and/or TLR4 as a marker for determining the clinical outcome of a subject suffering from an ectatic disease of the cornea.

Finally, the invention relates the invention relates to the use of TLR2 and/or TLR4 as a marker for selecting a subject to be treated with a therapy for an ectatic disease of the cornea or for selecting a refractive surgery as therapy for a subject suffering from a refractive defect.

The terms "TLR2", "TLR4", "diagnosis", "determining the risk", "determining the clinical outcome", "selecting a subject to be treated with therapy", "ectatic disease of the cornea" and their particulars and preferred embodiments have been previously defined in defined in the context of the first, second, third and fourth method of the invention and are equally applicable to the uses of the invention.

Method for Determining the Risk that a Patient Suffers Ectasia Following Refractive Surgery In another aspect, the invention relates to an in vitro method for determining the risk that a patient suffers ectasia following refractive surgery which comprises:
  a) determining the expression level of TLR2 and/or TLR4 in a sample from said subject; and
  b) comparing said expression level with a reference value wherein if the expression level of TLR2 and/or TLR4 is higher than said reference value is indicative that said subject shows high risk of suffering ectasia following refractive surgery.

In a preferred embodiment, the method of the invention comprises determining the expression level of TLR2 and TLR4 in a sample from the subject under study.

The term "refractive surgery" as used herein refers to any eye surgery used to improve the refractive state of the eye based on remodeling the curvature of the cornea.

The first step of the fifth method of the invention comprises determining the expression levels of TLR2 and/or TLR4 in a sample for the subject under study.

The terms "subject", "sample" and "refractive defect" have been previously defined in the context of the first method of the invention and are equally applicable to the fifth method of the invention.

In a particular embodiment, the sample from said subject is selected from conjunctival and corneal tissue. Methods for obtaining samples from conjunctival and corneal tissues have been detailed in the first method of the invention.

In a particular embodiment, the determination of the expression level of the TLR2 and/or TLR4 protein is carried out by immunohistochemistry or ELISA or protein array. In a preferred embodiment, the expression level of TLR2 and/or TLR4 is determined by flow cytometry.

The second step of the fifth method of the invention comprises comparing the expression levels of TLR2 and/or TLR4 with a reference value. The term "reference value" has been previously defined.

Once the comparison is made between the expression level of TLR2 and/or TLR4 in the sample from the subject under study and the reference value, the fourth method of the invention allows selecting a subject to be treated with a therapy for an ectatic disease of the cornea based on if the expression level of TLR2 and/or TLR4 is higher than said reference value. The terms "higher than", "less than" and "equal to" have been previously defined.

The Present Invention is also Directed To:
1. An in vitro method for diagnosing an ectatic disease of the cornea in a subject which comprises:
   a) determining the expression level of TLR2 and/or TLR4 in a sample from said subject; and
   b) comparing said expression level with a reference value wherein, if the expression level of TLR2 and/or TLR4 is higher than said reference value is indicative that the subject suffers from an ectatic disease of the cornea.
2. The in vitro method according to aspect 1 wherein said ectatic disease of the cornea is selected from subclinical keratoconus, clinical keratoconus, pellucid marginal degeneration, keratoglobus and ectasia post refractive corneal surgery.
3. The in vitro method according to aspect 2, wherein said ectatic disease of the cornea is subclinical keratoconus, in which case the reference value corresponds to the expression levels of TLR2 and/or TLR4 measured in a sample from a healthy subject.
4. The in vitro method according to aspect 2, wherein said ectatic disease of the cornea is clinical keratoconus, in which case the reference value corresponds to the expression levels of TLR2 and/or TLR4 measured in a sample from a subject suffering from subclinical keratoconus.
5. The in vitro method according to aspect 2, wherein said ectatic disease of the cornea is pellucid marginal degeneration, in which case the reference value corresponds to the expression levels of TLR2 and/or TLR4 measured in a sample from a healthy subject.
6. The in vitro method according to aspects 1 to 5, wherein the sample from said subject is selected from conjunctival and corneal tissue.
7. The in vitro method according to aspects 1 to 6, wherein said expression level comprises determining the level of mRNA encoded from the TLR2 and/or TLR4 gene or determining the level of the TLR2 and/or TLR4 protein.
8. The in vitro method according to aspect 7, the protein level is determining by immunohistochemistry, Western blot, flow cytometry or by ELISA.
9. The in vitro method of aspects 1 to 8 which also comprises determining at least one parameter selected from: diopters, corneal thickness and corneal elevation.
10. An in vitro method for determining the risk of developing an ectatic disease of the cornea in a subject which comprises:
    a) determining the expression level of TLR2 and/or TLR4 in a sample from said subject; and
    b) comparing said expression level with a reference value.
    wherein, if the expression level of TLR2 and/or TLR4 is higher than said reference value is indicative that the subject has high risk of developing an ectatic disease of the cornea.
11. The in vitro method according to aspect 10, wherein the subject has been previously diagnosed as having a refractive defect.
12. The in vitro method according to aspect 10 or 11, wherein said subject has developed a previous ocular pathology selected from: ocular itching, eye rubbing, biomicroscopic signs and conjunctival hyperemia.
13. An in vitro method for determining the clinical outcome of a subject suffering from an ectatic disease of the cornea, comprising:
    a) determining the expression level of TLR2 and/or TLR4 in a sample from said subject; and
    b) comparing said expression level with a reference value
    wherein if the expression level of TLR2 and/or TLR4 is higher than said reference value is indicative of a negative clinical outcome.
14. An in vitro method for selecting a subject to be treated with a therapy for an ectatic disease of the cornea which comprises:
    a) determining the expression level of TLR2 and/or TLR4 in a sample from said subject; and
    b) comparing said expression level with a reference value
    wherein if the expression level of TLR2 and/or TLR4 is higher than said reference value is indicative that said subject is candidate to be treated with a therapy for an ectatic disease of the cornea.
15. An in vitro method according to aspect 14 wherein said therapy is selected from corneal crosslinking, intracorneal rings and refractive surgery.
16. An in vitro method for selecting a refractive surgery as therapy for a subject suffering from a refractive defect which comprises:
    a) determining the expression level of TLR2 and/or TLR4 in a sample from said subject; and
    b) comparing said expression level with a reference value
    wherein if the expression level of TLR2 and/or TLR4 is higher than said reference value is indicative that said subject is not candidate to be treated with a refractive surgery for said refractive defect.
17. The in vitro method according to any of aspects 10 to 16, wherein said ectatic disease of the cornea is selected from subclinical keratoconus, clinical keratoconus, pellucid margin degeneration, keratoglobus and ectasia post refractive corneal surgery.
18. The in vitro method according to aspects 10 to 17, wherein the sample from said subject is selected from conjunctival and corneal tissue.
19. The in vitro method according to aspects 10 to 18, wherein said expression level comprises determining the level of mRNA encoded from the TLR2 and/or TLR4 gene or determining the level of the TLR2 and/or TLR4 protein.

20. The in vitro method according to aspect 19, the protein level is determining by immunohistochemistry, Western Blot, flow cytometry or ELISA.

21. Use of TLR2 and/or TLR4 as a marker for determining the diagnosis of an ectatic disease of the cornea in a subject, for determining the risk of developing an ectatic disease of the cornea in a subject, as a marker for determining the clinical outcome of a subject suffering from an ectatic disease of the cornea or as a marker for selecting a subject to be treated with a therapy for an ectatic disease of the cornea.

The following example is provided as merely illustrative and is not to be construed as limiting the scope of the invention.

EXAMPLES

Materials and Methods

We have included 2 different cohorts of patients:
1) In a cohort A we have included unilateral KC patients and control subjects in order to test whether TLR2 and TLR4 expression in cells of the corneal epithelium and bulbar conjunctiva of patients with pathological or clinical KC is greater than in subclinical KC, and higher than in samples from control subjects.
2) In a cohort B we have included bilateral KC patients, relatives of patients, PMD patients and control subjects in order to test whether TLR2 and TLR4 expression in cells of the corneal epithelium and bulbar conjunctiva of patients with pathological or clinical KC is greater than in their relatives, and higher than in samples from control subjects. Likewise, we tested whether TLR2 and TLR4 expression in cells of the corneal epithelium and bulbar conjunctiva of PMD patients is greater than in control subjects.

Patients and Control Subjects in Cohort A

We have designed a prospective, cross sectional study in which 50 unilateral KC patients (50 KC and 50 subclinical KC eyes) and 19 control subjects (38 eyes) were enrolled. Unilateral KC patients (64% males; mean age, 33.3±9.5 years) were selected from a database of KC patients at Servizo Galego de Saúde, Complexo Hospitalario de Santiago de Compostela, Spain. We studied both eyes from each patient or control subject. Patients were asked not to wear their contact lenses for a week prior to the study. Control (45.9% males; mean age, 28.5±4.7 years) subjects had not previous history of KC or eye rubbing, and no topographic alterations. All patients and control subjects were expressly cited for the purposes of this study, and all examinations were performed by the same researcher. Data collected included gender, age, patient's ocular history, medical history (allergy, eye rubbing), and history of KC. This research was carried out in accordance with the Declaration of Helsinki of the World Medical Association (2008) and approved by the Ethics Committee of Research at Servizo Galego de Saúde. Informed consent was obtained from each patient or control subject after full explanation of the procedures.

Inclusion criteria were: 1) Asymmetric KC patients (1 KC eye and 1 subclinical KC eye). Rabinowitz/McDonnell criterion was used for the KC diagnosis (Rabinowitz Y. S. Keratoconus. Surv. Ophthalmol. 1998; 42:297-319). According to the videokeratographic guidelines proposed by Rabinowitz & McDonnell, it is possible to classify an eye as subclinical keratoconus if the simulated central corneal power is greater than 47.2 D but less than 48.7 D, with an inferior-superior dioptric asymmetry greater than 1.4 D, but less than 1.9 D. Eyes presenting central corneal curvature exceeding 48.7 D, as well as inferior-superior dioptric asymmetry greater than 1.9 D can be classified as "true keratoconus"; 2) The distance visual acuity (DVA) of the subclinical KC eye with value of 1.0 (without correction or with spherical and/or cylindrical compensation<1.50 D).

Exclusion criteria included: 1) Previous surgical intervention in the anterior segment, or childhood corneal trauma or corneal-conjunctival disease; 2) Existence of active or systemic inflammation, or ocular disease, or current treatment with systemic or local anti-inflammatory drugs; 3) Hepatic, renal, hematologic, and immunologic diseases, disorders of thyroid function, uncontrolled diabetes, infections in the days preceding to the sample collection and solid tumors; as they may interfere with the results of the study of molecular markers of innate immunity.

Patients and Control Subjects in Cohort B

We have designed a prospective, cross sectional study in which 53 bilateral KC patients (106 KC eyes), 24 relatives (48 eyes), 13 PMD patients (26 eyes) and 34 control subjects (68 eyes) were enrolled. Bilateral KC patients (56% males; mean age, 33.3±8.4 years) and PMD patients (69% males; mean age, 47.7±8.9 years) were selected from a database of ectatic corneal patients at Servizo Galego de Saúde, Complexo Hospitalario de Santiago de Compostela, Spain. Relatives (52% males; mean age, 26.7±9.9 years) subjects had family history of KC, but no topographic alterations. Control subjects (41% males; mean age, 30.5±9.6 years) had not family history of KC or eye rubbing, and no topographic alterations. We studied both eyes from each KC or PMD patient, relative or control subject. Patients, relatives and control subjects were asked not to wear their contact lenses for a week prior to the study. All patients and control subjects were expressly cited for the purposes of this study, and the same researcher performed all examinations. Data collected included gender, age, patient's ocular history, medical history (allergy, eye rubbing), and family history of KC. This research was carried out in accordance with the Declaration of Helsinki of the World Medical Association (2008) and approved by the Ethics Committee of Research at Servizo Galego de Saúde. Informed consent was obtained from each patient or control subject after full explanation of the procedures.

Inclusion criteria were: 1) Bilateral KC patients (2 KC eyes). Rabinowitz/McDonnell criterion was used for the KC diagnosis (Rabinowitz Y. S. Keratoconus. Surv. Ophthalmol. 1998; 42:297-319). According to the videokeratographic guidelines proposed by Rabinowitz & McDonnell, it is possible to classify an eye as subclinical keratoconus if the simulated central corneal power is greater than 47.2 D but less than 48.7 D, with an inferior-superior dioptric asymmetry greater than 1.4 D, but less than 1.9 D. Eyes presenting central corneal curvature exceeding 48.7 D, as well as inferior-superior dioptric asymmetry greater than 1.9 D can be classified as "true keratoconus"; 2) The distance visual acuity (DVA) of the subclinical KC eye with value of 1.0 (without correction or with spherical and/or cylindrical compensation<1.50 D). 2) PMD patients (2 KC eyes). PMD was considered when we identified a marked central corneal flattening along the vertical axis with severe against-the-rule astigmatism and marked steepening of the inferior peripheral cornea and typically shows a crab-claw pattern. 3) Relatives: first-degree relative of patients with ectatic disorders (PMD or KC) but without topographic alterations.

Exclusion criteria included: 1) Previous surgical intervention in the anterior segment, or childhood corneal trauma or corneal-conjunctival disease; 2) Existence of active or systemic inflammation, or ocular disease, or current treatment with systemic or local anti-inflammatory drugs; 3) Hepatic, renal, hematologic, and immunologic diseases, disorders of thyroid function, uncontrolled diabetes, infections in the days preceding to the sample collection and solid tumors; as they may interfere with the results of the study of molecular markers of innate immunity.

Clinical variables

Epidemiological variables: age, gender, KC year of diagnosis, personal and family history, Therapeutic variables: antihistamines, systemic or local anti-inflammatory or antibiotic.

Variables associated to KC: ocular itching and its intensity, eye rubbing and its intensity, AVL and AVP with and without optical correction, biomicroscopical signs, conjunctival hyperemia scale, Schirmer test, contact lens wear.

Topographic variables: PDC (simK), K max, K min, K1, K2, Ka, Dk, MPD and distance to the center. Classification of Krumeich and Classification of CLEK for the KC grade. Elevation and aberrometric values.

Study Groups

For comparative analysis, we have defined the following groups:

Cohort A:
Group 1: controls without topographical alterations.
Group 2: subclinical KC.
Group 3: KC.

Cohort B:
Group 1: controls without topographical alterations.
Group 2: Bilateral KC.
Group 3: PMD.
Group 4: relatives without topographical alterations.

These groups were established in order to determine the predictive value of TLRs as a biomarker of risk for onset or progression of KC or PMD.

Instrumental

Basic examination instruments were a Topcon biomicroscope, Topcon refraction column, and alphabetic Snellen visual acuity test. As specific examination instruments we used a TOPCON CA-100 System (Topcon Medical Systems, Inc., NJ, USA), and an Orbscan II corneal topographer (Orbtek, Utah, USA).

Procedure

Our protocol collected the following information: elapsed time from diagnosis of KC in the first eye, laterality, itching and rubbing, family history of KC and allergies.

After obtaining the best correction, the biomicroscopy exam was performed to detect signs of KC. The corneal topography study was performed using the TOPCON and the Orbscan topographers. Five quantitative topographic parameters were analyzed: simulated keratometry (K) readings, posterior elevation and the thinnest point pachymetry of the cornea.

TLR2 and TLR4 Expression Analysis

TLR2 and 4 expression analyses were performed by flow cytometry in conjunctival and corneal cells, withdrawn from all control subjects and subclinical KC patients by means of a PVA foam surgical spear (SOFT CELL®, OASIS®, CA, USA). For the expression analysis of TLR2 and TLR4, conjunctival and corneal cells were separated by their forward and side scattering signal characteristics. FITC-TLR2 antibody (IMMUNOSTEP, Salamanca, Spain) and PE-TLR4 antibody (IMMUNOSTEP, Salamanca, Spain) were used to quantify TLR expression. Samples were analyzed on a FACSAria flow cytometer (BD Biosciences, NJ, USA). Cell fluorescence was measured immediately after staining, and data were analyzed with the use of FACSDiva software (BD Biosciences, NJ, USA). For cohort A, mean expression of TLR2 and TLR4 in conjunctival (1250 events) and corneal cells (500 events) was analyzed and expressed as AFU (arbitrary fluorescence units). For cohort B, mean expression of TLR2 and TLR4 in conjunctival (2000 events) and corneal cells (1000 events) was analyzed and expressed as AFU (arbitrary fluorescence units).

Statistical Analysis

The results were expressed as percentages for categorical variables and as mean (SD) or median [quartiles] for the continuous variables depending on their normal distribution or not, respectively. The Kolmogorov-Smirnov test was used for testing the normality of the distribution. Proportions were compared using the chi-square test, while the continuous variables between groups were compared with the Student's t-(variables with normal distribution) or the Mann-Whitney (variables with non-normal distribution) tests. ANOVA was used to analyze the relationship between study groups and TLR2 and TLR4 in corneal and conjunctival cells. Receiver operating characteristic (ROC) curves were configured to establish cut-off points of TLR2 and TLR4 in corneal and conjunctival cells that optimally predicted risk of appearance or progression of KC or PMD. A value of $p<0.05$ was considered to be statistically significant. The statistical analysis was conducted using SPSS 16.0 for Mac.

Example 1

Clinical Features for Cohort A

No gender-related statistical differences were detected between the study groups, however patients with KC were older and sowed more frequent history of KC (Table 1). The elapsed time from the first diagnosis of KC eye ranged from 1 to 30 years (mean, 8.3±6.2 years). Twenty-three KC patients (46%) and 19 control subjects (51.4%) reported allergy disease and 15 KC patients (30%) a family history of KC. Thirteen control subjects (35.1%) and 31 patients (62%) reported itchy eyes. For patients who reported itchy eyes, 71% admitted frequent and vigorous eye rubbing on the KC eye. Thirteen control subjects (35.1%) also reported eye rubbing.

Table 1 shows the mean K2 values for all study groups. Mean K2 was higher in the KC eye versus the other study groups ($p<0.0001$).

Descriptive Study

TABLE 1

Baseline clinical characteristics and TLR conjunctival and corneal cell expression in study groups of cohort A.

| Variable | Control | Subclinical KC | KC | p value |
|---|---|---|---|---|
| Age (years) | 28.5 ± 4.7 | 33.3 ± 9.5 | 33.3 ± 9.5 | 0.029 |
| Gender (% males) | 45.9 | 64.0 | 64.0 | 0.538 |
| History of KC (%) | 0 | 30.0 | 30.0 | 0.002 |

TABLE 1-continued

Baseline clinical characteristics and TLR conjunctival and corneal cell expression in study groups of cohort A.

| Variable | Control | Subclinical KC | KC | p value |
|---|---|---|---|---|
| Central K (diopters) | 43.4 [41.8-45.3] | 43.6 [42.3-44.7] | 48.1 [45.1-52.1] | <0.0001 |
| Minimum thickness point (μm) | 552.0 [513.5-567.0] | 519.0 [487.5-546.0] | 480.0 [417.0-502.0] | <0.0001 |
| Posterior elevation (μm) | 0.038 [0.024-0.036] | 0.036 [0.029-0.047] | 0.089 [0.062-0.122] | <0.0001 |
| K2 (diopters) | 43.7 [42.3-45.3] | 44.0 [43.0-44.8] | 48.0 [46.4-50.5] | <0.0001 |
| TLR2 conjunctiva (AFU) | 213 [90-295] | 207 [124-398] | 422 [178-1065] | <0.0001 |
| TLR4 conjunctiva (AFU) | 1581 [1281-2265] | 1922 [1574-2778] | 2377 [1817-3032] | <0.0001 |
| TLR2 cornea (AFU) | 185 [113-286] | 977 [647-1330] | 2569 [2071-3808] | <0.0001 |
| TLR4 cornea (AFU) | 1654 [1134-2587] | 2569 [2071-3808] | 4125 [3233-5076] | <0.0001 |

Values are expressed in median [quartiles].
KC: Keratoconus;
TLR2: Toll-Like Receptor 2);
TLR4: Toll-Like Receptor 4);
AFU: Arbitrary Fluorescence Unit TLR2 and TLR4 Expression in Corneal and Conjunctival Cells for Cohort A Levels of TLR2 and TLR4 expression in KC, subclinical KC and control groups in both corneal and conjunctival cells are also shown in table 1. TLR2 and TLR4 expression in both corneal and conjunctival cells was higher in the KC groups. Moreover, the higher the expression of TLR2 and TLR4 was the higher the progression of KC (table 1). However, the main difference of TLR expression from the control groups to subclinical KC and KC groups was found for the expression of TLR2 and TLR4 in corneal cells. Therefore, predictive analyses were focused exclusively on the expression of TLR2 and TLR4 in corneal cells.

Predictive Value of TLR2 and TLR4 Expression in Corneal Cells for Risk of Onset and Progress to KC for Cohort A According to the ROC analysis, TLR2 expression in corneal epithelial cells may predict with high sensitivity and specificity the probability of KC (both subclinical KC and KC) compared to the controls (area under the curve 0.995, 95% CI: 0.987-1.000; p<0.0001). Likewise, TLR2 expression in corneal cells is also useful for predicting with high sensitivity and specificity the probability of subclinical KC compared to the controls (area under the curve 0.989, 95% CI: 0.975-1.000; p<0.0001). Finally, corneal TLR2 expression also predict with the high sensitivity and specificity the probability of no subclinical KC compared to the KC (area under the curve 0.893, 95% CI: 0.834-0.953; p<0.0001). In summary, table 2 shows the sensitivity and specificity for the utility of several cut-off points for TLR2 expression in corneal cells for detecting the risk of onset and progression of KC.

On the other hand, according to the ROC analysis, TLR4 expression in corneal epithelial cells may also predict with high sensitivity and specificity the probability of KC (both subclinical KC and KC) compared to the controls (area under the curve 0.846, 95% CI: 0.776-0.915; p<0.0001). Likewise, TLR4 expression in corneal cells is also useful for predicting with high sensitivity and specificity the probability of subclinical KC compared to the controls (area under the curve 0.756, 95% CI: 0.653-0.860; p<0.0001). Finally, corneal TLR4 expression also predict with the high sensitivity and specificity the probability of no subclinical KC compared to the KC (area under the curve 0.767, 95% CI: 0.673-0.860; p<0.0001). Table 3 shows the sensitivity and specificity for the utility of several cut-off points for TLR4 expression in corneal cells for detecting the risk of onset of progression of KC.

In conclusion, TLR2 expression in corneal cells showed higher predictive value for detecting the risk of onset and progression of KC than the expression of TLR4.

TABLE 2

Sensitivity and specificity values for the utility of TLR2 expression in corneal cells for detecting the risk of onset of progression of KC for cohort A.

| TLR2 expression (AFU) | SENSITIVITY | SPECIFICITY |
|---|---|---|
| Control vs. KC patients (Subclinical KC + KC) | | |
| <330 AFU | 99% | 84% |
| 330-660 AFU | 89-98% | 85-99% |
| >660 AFU | 88% | 100% |
| Control vs. Subclinical KC | | |
| <330 AFU | 98% | 84% |
| 330-660 AFU | 75-97% | 85-99% |
| >660 AFU | 74% | 100% |
| Subclinical KC vs. KC | | |
| <330 AFU | 100% | 2% |
| >660 AFU | 100% | 26% |
| 660-1500 AFU | 69-99% | 27-87% |
| >1500 AFU | 68% | 88% |

TABLE 3

Sensitivity and specificity values for the utility of TLR4 expression in corneal cells for detecting the risk of onset of progression of KC for cohort A.

| TLR4 expression (AFU) | SENSITIVITY | SPECIFICITY |
|---|---|---|
| Control vs. KC patients (Subclinical KC + KC) | | |
| <1500 AFU | 94% | 46% |
| 1500-4000 AFU | 36-93% | 45-96% |
| >4000 AFU | 35% | 97% |
| Control vs. Subclinical KC | | |
| <1500 AFU | 88% | 46% |
| 1500-4000 AFU | 23-87% | 45-96% |
| >4000 AFU | 22% | 97% |

TABLE 3-continued

Sensitivity and specificity values for the utility
of TLR4 expression in corneal cells for detecting the
risk of onset of progression of KC for cohort A.

| TLR4 expression (AFU) | SENSITIVITY | SPECIFICITY |
|---|---|---|
| Subclinical KC vs. KC | | |
| <1500 AFU | 100% | 22% |
| >4000 AFU | 520% | 80% |
| >5000 AFU | 28% | 90% |

Correlation Between TLR2 and TLR4 Expression in Corneal Cells and Clinical Parameters of KC Progression (K2 and Kc) for Cohort A The expression levels of TLR2 and TLR4 were analyzed in cornea cells from clinical and subclinical KC patients regarding two quantitative parameters related to the progression of keratoconus, namely K2 and Kc. A simpler linear regression analysis was made calculating bivariate correlations with Pearson test. The results are expressed as correlation coefficient r:

K2
TLR2; r=0.525; p<0.0001
TLR4; r=0.359; p<0.001
Kc
TLR2; r=0.439; p<0.0001
TLR4; r=0.379; p<0.0001

These results confirm an association between TLR2 and TLR4 expression in corneal cells with the progression and the severity of subclinical and clinical KC.

Example 2

Clinical Features for Cohort B

No gender-related statistical differences were detected between the study groups, however patients with PMD were older and KC patients showed more frequent history of ectatic disorders than control subjects and PMD patients (table 4). Twenty-eight KC patients (65%), 6 PMD patients (46%), 9 relatives (39%) and 14 control subjects (41.2%) reported allergy disease. Likewise, the 88% of KC patients, 84% of PMD patients, 39% of relatives and 26% of control subjects reported itchy eyes. For patients who reported itchy eyes, the 76% of KC patients, 76% of PMD patients, 35% of relatives and 35% of control subjects admitted frequent and vigorous eye rubbing on the KC eye.

Table 4 shows the median K2, central K, minimum thickness point and posterior elevation values for all study groups. Median K2 and central K were higher in the KC eyes versus the other study groups (p<0.0001). Likewise, posterior elevation was higher in the KC and PMD eyes versus control and relative subjects (p<0.0001). By contrast, the minimum thickness point was lower for KC and PMD eyes compared to the other groups (p<0.0001).

TABLE 4

Baseline clinical characteristics and TLR conjunctival and corneal cell expression in study groups of cohort B.
DESCRIPTIVE STUDY

| Variable | Control | PMD | KC | Relatives | p value |
|---|---|---|---|---|---|
| Age (years) | 30.5 ± 9.6 | 47.7 ± 8.9 | 33.3 ± 8.4 | 26.7 ± 9.9 | <0.0001 |
| Gender (% males) | 41.2 | 69.2 | 55.8 | 52.2 | 0.335 |
| History of KC (%) | 0 | 7.7 | 25.6 | 100 | <0.0001 |
| Central K (diopters) | 44.0 [42.7-45.3] | 43.5 [41.1-45.5] | 47.8 [44.2-51.7] | 44.3 [43.7-45.0] | <0.0001 |
| Minimum thickness point (μm) | 560.0 [536.0-582.5] | 496.5 [410.8-544.0] | 471.0 [400.0-509.0] | 544.5 [512.5-573.0] | <0.0001 |
| Posterior elevation (μm) | 0.029 [0.021-0.038] | 0.085 [0.049-0.107] | 0.087 [0.056-0.117] | 0.027 [0.019-0.037] | <0.0001 |
| K2 (diopters) | 44.4 [43.0-45.8] | 45.5 [44.1-50.8] | 48.6 [45.5-51.7] | 44.5 [43.7-45.2] | <0.0001 |
| TLR2 conjunctiva (AFU) | 733 [560-946] | 815 [669-1163] | 1184 [943-1491] | 1178 [655-1441] | <0.0001 |
| TLR4 conjunctiva (AFU) | 2380 [1781-3283] | 4080 [3392-4610] | 4230 [3496-5163] | 3331 [2702-4000] | <0.0001 |
| TLR2 cornea (AFU) | 580 [413-976] | 743 [639-1106] | 1782 [1254-3119] | 891 [575-1316] | <0.0001 |
| TLR4 cornea (AFU) | 1572 [949-2353] | 2251 [1711-2982] | 3812 [2774-5408] | 1904 [1466-2522] | <0.0001 |

Values are expressed in median [quartiles].

KC: Keratoconus;

PMD: Pellucid marginal degeneration;

TLR2: Toll-Like Receptor 2;

TLR4: Toll-Like Receptor 4;

AFU: Arbitrary Fluorescence Units.

TLR2 and TLR4 Expression in Corneal and Conjunctival Cells for Cohort B

Levels of TLR2 and TLR4 expression in KC, PMD, relatives and control groups in both corneal and conjunctival cells are also shown in table 4. TLR2 and TLR4 expression in both corneal and conjunctival cells was higher in the KC group respect to the other groups. Moreover, PMD group also showed higher expression of TLR2 in corneal cells and TLR4 in both corneal and especially conjunctival cells than the control group (table 4). Interestingly, relatives showed higher expression of TLR2 and TLR4 in both corneal and conjunctival cells than control subjects, but this expression is much lower than in patients KC (table 4). However, the main difference of TLR expression from the control group to KC group was found for the expression of TLR2 and TLR4 in corneal cells. On the other hand, the main difference of TLR expression from the control group to PMD group was found for the expression of TLR4 in conjunctival cells. Therefore, predictive analyses were focused exclusively on the expression of TLR2 and TLR4 in corneal cells for KC, and TLR4 in conjunctival cells for PMD.

Predictive Value of TLR2 and TLR4 Expression in Corneal Cells for Risk of Onset and Progress to KC for Cohort B According to the ROC analysis, TLR2 expression in corneal epithelial cells may predict with high sensitivity and specificity the probability of KC compared to the controls (area under the curve 0.874, 95% CI: 0.815-1.000; p<0.0001). Likewise, TLR2 expression in corneal cells is also useful for predicting with high sensitivity and specificity the probability of KC compared to relatives (area under the curve 0.802, 95% CI: 0.723-0.882; p<0.0001). In summary, table 5 shows the sensitivity and specificity for the utility of several cut-off points for TLR2 expression in corneal cells for detecting the risk of onset and progression of KC.

On the other hand, according to the ROC analysis, TLR4 expression in corneal epithelial cells may also predict with high sensitivity and specificity the probability of KC compared to the controls (area under the curve 0.877, 95% CI: 0.818-0.936; p<0.0001). Likewise, TLR4 expression in corneal cells is also useful for predicting with high sensitivity and specificity the probability of KC compared to relatives (area under the curve 0.882, 95% CI: 0.821-0.943; p<0.0001).

TABLE 5

Sensitivity and specificity values for the utility of TLR2 expression in corneal cells for detecting the risk of onset or progression of KC in cohort B.

| TLR2 expression (AFU) | SENSITIVITY | SPECIFICITY |
|---|---|---|
| Control subjects vs. KC patients | | |
| <327 AFU | 99% | 86% |
| 327-1269 AFU | 75-98% | 76-91% |
| >1269 AFU | 89% | 92% |
| Relatives vs. KC patients | | |
| <521 AFU | 95% | 84% |
| 521-1352 AFU | 71-94% | 28-88% |
| >1352 AFU | 71% | 91% |

Table 6 shows the sensitivity and specificity for the utility of several cut-off points for TLR4 expression in corneal cells for detecting the risk of onset of progression of KC.

In conclusion, TLR2 and TLR4 expression in corneal cells showed a high predictive value for detecting the risk of onset and progression of KC.

TABLE 6

Sensitivity and specificity values for the utility of TLR4 expression in corneal cells for detecting the risk of onset or progression of KC in cohort B.

| TLR4 expression (AFU) | SENSITIVITY | SPECIFICITY |
|---|---|---|
| Control subjects vs. KC patients | | |
| <1508 AFU | 95% | 53% |
| 1508-4000 AFU | 42-94% | 52-96% |
| >4000 AFU | 41% | 97% |
| Relatives vs. KC patients | | |
| <1697 AFU | 95% | 41% |
| 1697-3794 AFU | 51-99% | 42-99% |
| >3794 AFU | 50% | 100% |

Predictive Value of TLR4 Expression in Conjunctival Cells for Risk of Onset and Progress to PMD for Cohort B Finally, according to the ROC analysis, TLR4 expression in conjunctival epithelial cells may also predict with high sensitivity and specificity the probability of PMD compared to the control subjects (area under the curve 0.823, 95% CI: 0.733-0.913; p<0.0001). Table 7 shows the sensitivity and specificity for the utility of several cut-off points for TLR4 expression in conjunctival cells for detecting the risk of onset of progression of KC.

In conclusion, TLR4 expression in conjunctival cells showed also high predictive value for detecting the risk of onset and progression of PMD.

TABLE 7

Sensitivity and specificity values for the utility of TLR4 expression in conjunctival cells for detecting the risk of onset or progression of PMD in cohort B.
Control subjects vs. PMD patients

| TLR4 expression (AFU) | SENSITIVITY | SPECIFICITY |
|---|---|---|
| <1543 AFU | 100% | 82% |
| 1543-4500 AFU | 31-99% | 52-92% |
| >4500 AFU | 31% | 93% |

Correlation Between TLR2 and TLR4 Expression in Corneal Cells and Clinical Parameters of KC Progression (K2, Kc and Kmax) for Cohort B We analyzed the expression levels of TLR2 and TLR4 in corneal cells from KC patients regarding three quantitative parameters related to the progression of keratoconus, namely K2, Kc and Kmax and made a simpler linear regression analysis calculating bivariate correlations with Pearson test. The results are expressed as correlation coefficient (r):

K2
TLR2; $r=0.286$; $p<0.0001$
TLR4; $r=0.249$; $p<0.0001$
Kc
TLR2; $r=0.266$; $p<0.0001$
TLR4; $r=0.286$; $p<0.0001$
Kmax
TLR2; $r=0.403$; $p<0.0001$
TLR4; $r=0.263$; $p<0.0001$ These results confirm an association between TLR2 and TLR4 expression in corneal cells with the progression and the severity of KC.

Correlation Between TLR4 Expression in Conjunctival Cells and Clinical Parameters of PMD Progression (Kmax) for Cohort B On the other hand, we also analyzed the expression levels of TLR4 in conjunctival cells from PMD patients regarding Kmax, a parameter related to the progression of PMD. We made a simpler linear regression analysis calculating bivariate correlations with Pearson test. The results are expressed as correlation coefficient (r):

Kmax

TLR4; r=0.327; p<0.0001

In summary, these results also confirm an association between TLR4 expression in conjunctival cells with the progression and the severity of PMD.

The invention claimed is:

1. An in vitro method for diagnosing and treating an ectatic disease of the cornea in a subject, or for determining the clinical outcome of a subject suffering from an ectatic disease of the cornea and treating said subject, or for selecting a subject to be treated with a therapy for an ectatic disease of the cornea and treating said subject, said method comprising:
   a) obtaining a sample from said subject:
   b) determining the expression level of TLR2 and/or TLR4 in the sample from said subject;
   c) comparing said expression level with a reference value;
   d) diagnosing the subject with an ectatic disease of the cornea, or determining that the subject has a negative clinical outcome, or selecting a subject as a candidate to be treated with a therapy for an ectatic disease of the cornea when the expression level of TLR2 and/or TLR4 is higher than the reference value; and
   e) administering a therapy for treating an ectatic disease of the cornea to the subject identified in step (d), wherein said therapy is selected from the group consisting of corneal crosslinking, intracorneal rings, and refractive surgery.

2. The in vitro method according to claim 1 wherein said ectatic disease of the cornea is selected from subclinical keratoconus, clinical keratoconus, pellucid marginal degeneration, keratoglobus and ectasia post refractive corneal surgery.

3. The in vitro method according to claim 2, wherein said ectatic disease of the cornea is subclinical keratoconus, and the reference value corresponds to the expression levels of TLR2 and/or TLR4 measured in a sample from a healthy subject.

4. The in vitro method according to claim 2, wherein said ectatic disease of the cornea is clinical keratoconus, and the reference value corresponds to the expression levels of TLR2 and/or TLR4 measured in a sample from a subject suffering from subclinical keratoconus.

5. The in vitro method according to claim 2, wherein said ectatic disease of the cornea is pellucid marginal degeneration, and the reference value corresponds to the expression levels of TLR2 and/or TLR4 measured in a sample from a healthy subject.

6. The in vitro method according to claim 1, wherein the sample from said subject is selected from conjunctival and corneal tissue.

7. The in vitro method according to claim 1, wherein said expression level comprises determining the level of mRNA encoded from the TLR2 and/or TLR4 gene or determining the level of the TLR2 and/or TLR4 protein.

8. The in vitro method according to claim 7, wherein the protein level is determined by a method selected from immunohistochemistry, Western blot, flow cytometry or by ELISA.

9. The in vitro method for diagnosing an ectatic disease of the cornea in a subject according to claim 1 which also comprises determining at least one parameter selected from: diopters, corneal thickness and corneal elevation.

10. The in vitro method according to claim 1, wherein step (b) performed by contacting said sample with a composition or kit which comprises an antibody, a polypeptide, a primer and/or probe which specifically bonds to TLR2 and/or TLR4.

11. An in vitro method for determining whether a subject suffering from a refractive defect is a candidate for a refractive surgery therapy or for determining the risk that a subject suffers ectasia following refractive surgery and treating said subject with a suitable therapy, said method comprising:
   a) obtaining a sample from said subject;
   b) determining the expression level of TLR2 and/or TLR4 in a sample from said subject;
   c) comparing said expression level with a reference value;
   d) determining that said subject is not a candidate to be treated with a refractive surgery for said refractive defect, or determining that said subject shows high risk of suffering ectasia following refractive surgery when the expression level of TLR2 and/or TLR4 is higher than the reference value; and
   e) administering a therapy for treating a refractive defect other than refractive surgery to the subject identified in step (d), wherein said therapy is selected from the group consisting of corneal crosslinking and intracorneal rings.

12. The in vitro method according to claim 11, wherein the sample from said subject is selected from conjunctival and corneal tissue.

13. The in vitro method according to claim 11, wherein said expression level comprises determining the level of mRNA encoded from the TLR2 and/or TLR4 gene or determining the level of the TLR2 and/or TLR4 protein.

14. The in vitro method according to claim 13 wherein the protein level is determined by a method selected from immunohistochemistry, Western blot, flow cytometry or by ELISA.

* * * * *